US008293733B2

(12) United States Patent
Casaña Giner et al.

(10) Patent No.: US 8,293,733 B2
(45) Date of Patent: Oct. 23, 2012

(54) OIL DISPERSIONS OF NACHR BINDING NEONICOTINOIDS

(75) Inventors: Victor Casaña Giner, Ebenfurth (AT); Miguel Gimeno Sierra, Berndorf (AT); Bárbara Gimeno Sierra, Ebenfurth (AT)

(73) Assignee: GAT Microencapsulation AG (AT)

( * ) Notice: Subject to any disclaimer, the term of this patent is extended or adjusted under 35 U.S.C. 154(b) by 0 days.

(21) Appl. No.: 13/254,785

(22) PCT Filed: Mar. 4, 2010

(86) PCT No.: PCT/EP2010/001358
§ 371 (c)(1),
(2), (4) Date: Sep. 2, 2011

(87) PCT Pub. No.: WO2010/099965
PCT Pub. Date: Sep. 10, 2010

(65) Prior Publication Data

US 2012/0004104 A1 Jan. 5, 2012

(30) Foreign Application Priority Data

Mar. 5, 2009 (EP) .................................... 09003183

(51) Int. Cl.

| | |
|---|---|
| ***A61K 31/535*** | (2006.01) |
| ***A61K 31/435*** | (2006.01) |
| ***A61K 31/44*** | (2006.01) |
| ***A61K 31/34*** | (2006.01) |
| ***A61K 31/426*** | (2006.01) |
| ***A01N 43/08*** | (2006.01) |
| ***A01N 43/78*** | (2006.01) |

(52) U.S. Cl. ..................... 514/229.2; 514/277; 514/341; 514/342; 514/365; 514/461

(58) Field of Classification Search ........................ None
See application file for complete search history.

(56) References Cited

U.S. PATENT DOCUMENTS

2007/0066489 A1* 3/2007 Vermeer et al. ............... 504/363

FOREIGN PATENT DOCUMENTS

WO 96/33611 10/1996

OTHER PUBLICATIONS

Tadros, "Disperse Systems in Pesticidal Formulations," Advances in Colloid and Interface Science, vol. 32, Jan. 1, 1990, pp. 205-234.
Croda, Product Summary, Atlox 4912, retrieved from http://crop.crodadirect.com/print.aspx?view=dtl&d-contents&s-14 . . . on Nov. 8, 2009, 2 pages.
International Bureau, "International Search Report," issued in connection with PCT/EP2010/001358, completed Jun. 30, 2011, mailed Jul. 6, 2011, 3 pages.

* cited by examiner

*Primary Examiner* — Alton Pryor
(74) *Attorney, Agent, or Firm* — Vedder Price PC

(57) ABSTRACT

Selective insect neonicotinoids is a class of pesticide active ingredients that share some characteristics in their chemical structures and bind to the nAChR acetylcholine receptors. Formulation of such compounds in oil suspension or oil dispersion is challenging due to their electrostatic interactions of the heteroatoms in oily media, that lead to irreversible flocculation or diminished homogeneicity and bleeding of such oil dispersions. Imidacloprid, Thiamethoxam, Thiachloprid, Nitenpyram, Acetamiprid, Clothianidin and Dinetofuran and derivatives thereof with nAChR binding ability are successfully formulated in oil suspension with the use of certain copolymeric anionic fatty-acid based dispersants, sorbitan derivatives, ionic surfactants, other non-ionic surfactants and inorganic polyvalent cationic salt dispersed in the oil. The formulations this way produced show excellent storage stability properties regarding physiochemical parameters, including stability of the neonicotinoid active ingredient, reduced bleeding, and complete redispersibility. Further, they show excellent biological efficacy due to the reduced and homogeneous particle size below 2 μm when diluted—emulsified—in water.

14 Claims, No Drawings

OIL DISPERSIONS OF NACHR BINDING NEONICOTINOIDS

The present invention refers on one side to the control of pests, predominantly insects, fleas, ticks and mites, in agriculture or veterinary, by the use of certain neonicotinoids in the form of oil dispersion. It is the purpose of the present invention to prepare formulations of any neonicotinoids for improved physicochemical quality of the formulation, including the protection against degradation of the active ingredient(s), emulsion and storage stability properties while maintaining the biological activity. The solution has been found to be the use of a determined surfactant system containing particular non-ionic oil soluble dispersants of the type block copolymer and non-ionic dispersants polymeric polyhydroxyfatty acids with the concomitant use of salts of polyvalent cations, further containing sorbitan derivatives and fatty alcohol derivatives. Preferred mixtures of neonicotinods with other pesticides are disclosed.

Molecules

Selective insect neonicotinoids is a class of pesticide active ingredients that share some characteristics in their chemical structures and bind to the nAChR acetylcholine receptors.

The neonicotinoids disclosed in the present invention are all compounds with have the ability to be bound to the nAChR, preferably insect specific and not binding to mammal's acetylcholine receptors, either as molecules that bind without being metabolized prior to binding or that undergo a metabolic transformation (e.g., denitro and/or decyano derivatives) prior to binding. In general, the neonicotinoids will be active against insects, mites and fleas (Insecta and Acaricidae). Therefore their application ranges from the agricultural, veterinary, house and garden and even pharmaceutical field.

For, the control of pests, we perform a purposive selection of such neonicotinoids according the general formula (I):

A-(CH2)—B (I)

Wherein A is selected from

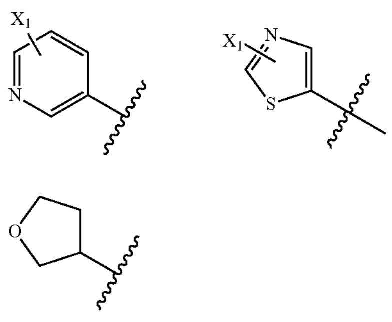

being X1 selected from the halogens chlorine, iodine, fluor, bromine; such halogen being attached to the heterocycle in any position except to the carbon atom that is bound to the (CH2) of compounds (I) (indicated by the curved line) and except to the heteroatom(s); and being possible the presence up to two additional halogen atoms X2 and X3 attached to the heterocycle in any of the resulting free positions;

and B is selected from

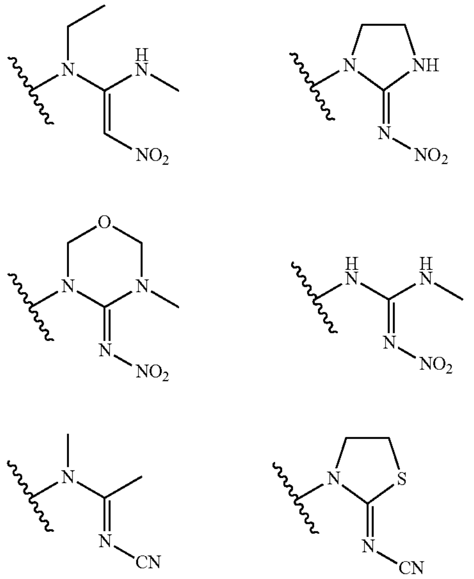

wherein the nitro or cyano group is in any stereochemical position, being shown just one of the two isomeric positions for nitro or cyano, and wherein the methyl groups may be replaced by trifuromethyl groups.

We disclose herein the preferred insecticide neonicotinoids for management of pests according the present invention:

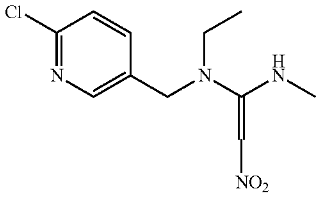

N′-((6-chloropyridin-3-yl)methyl)-N′-ethyl-N-methyl-2-nitroethene-1,1-diamine
or N-(6-chloro-3-pyridylmethyl)-N-ethyl-N′-methyl-2-nitrovinylidenediamine [for the E- isomer: NITENPYRAM]

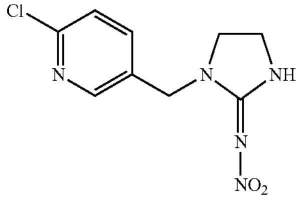

N-(1-((6-chloropyridin-3-yl)methyl)imidazolidin-2-ylidene)nitramide

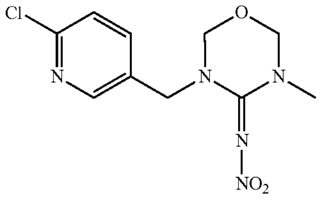

N-(3-((6-chloropyridin-3-yl)methyl)-5-methyl-1,3,5-oxadiazinan-4-ylidene)nitramide -continued

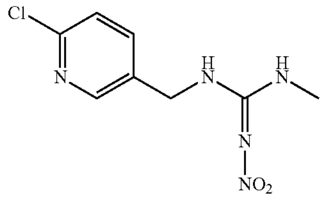

1-((6-chloropyridin-3-yl)methyl)-3-methyl-2-nitroguanidine

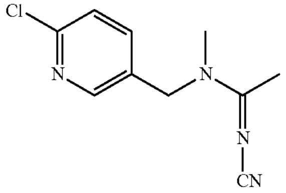

N-((6-chloropyridin-3-yl)methyl)-N′-cyano-N-methylacetimidamide or $N^1$-[((6-chloro-3-pyridyl)methyl]-$N^2$-cyano-$N^1$-methylacetamidine [for the E- isomer: ACETAMIPRID]

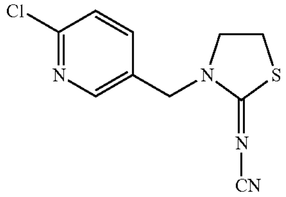

N-(3-((6-chloropyridin-3-yl)methyl)thiazolidin-2-ylidene)cyanamide or 3-(6-chloro-3-pyridylmethyl)-1,3-thiazolidin-2-ylidenecyanamide [for the Z-isomer: THIACLOPRID]

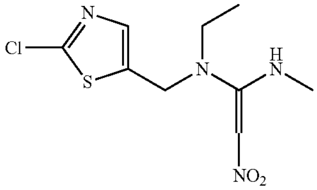

N′-ethyl-N-methyl-2-nitro-N′-(2-chlorothiazol-5-ylmethyl)ethene-1,1-diamine

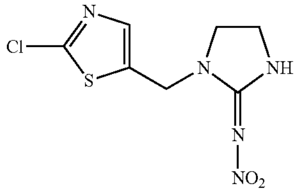

N-(1-((2-chlorothiazol-5-yl)methyl)imidazolidin-2-ylidene)nitramide

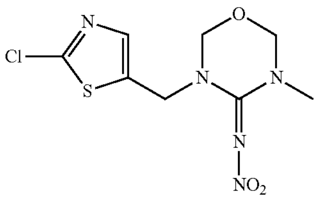

N-(3-((2-chlorothiazol-5-yl)methyl)-5-methyl-1,3,5-oxadiazinan-4-ylidene)nitramide or 3-(2-chloro-1,3-thiazol-5-ylmethyl)-5-methyl-1,3,5-oxadiazinan-4-ylidene(nitro)amine [THIAMETOXAM]

-continued

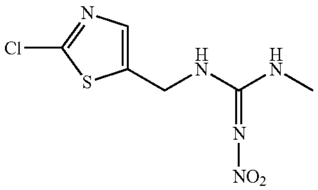

1-((2-chlorothiazol-5-yl)methyl)-3-methyl-2-nitroguanidine or 1-(2-chloro-1,3-thiazol-5-ylmethyl)-3-methyl-2-nitroguanidine

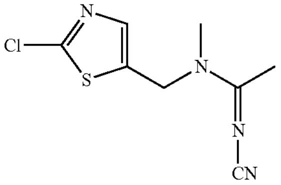

N-((2-chlorothiazol-5-yl)methyl)-N′-cyano-N-methylacetimidamide

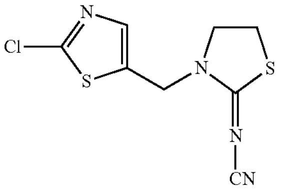

N-(3-((2-chlorothiazol-5-yl)methyl)thiazolidin-2-ylidene)cyanamide

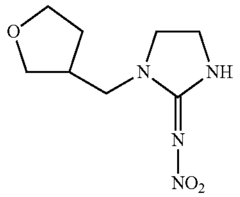

N-(1-((tetrahydrofuran-3-yl)methyl)imidazolidin-2-ylidene)nitramide

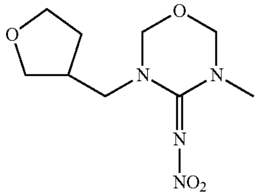

N-(3-methyl-5-((tetrahydrofuran-3-yl)methyl)-1,3,5-oxadiazinan-4-ylidene)nitramide

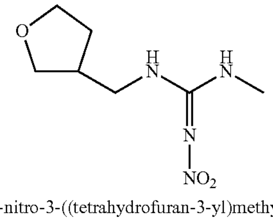

1-methyl-2-nitro-3-((tetrahydrofuran-3-yl)methyl)guanidine or (RS)-1-methyl-2-nitro-3-(tetrahydro-3-furylmethyl)guadine [DINETOFURAN]

-continued

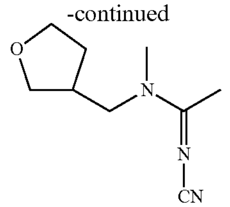

N'-cyano-N-methyl-N-((tetrahydrofuran-3-yl)methyl)acetimidamide

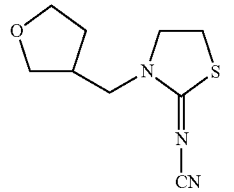

N-(3-((tetrahydrofuran-3-yl)methyl)thiazolidin-2-ylidene)cyanamide

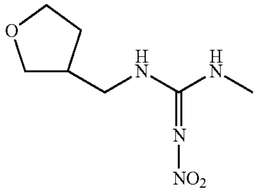

1-methyl-2-nitro-3-((tetrahydrofuran-3-yl)methyl)guanidine

In case of doubt, the chemical drawing should clearly stablish the chemical compound referred herein to. The names of the aforementioned compounds, has been given according the automatic nomenclature—except the prima note on some N atoms—provided by the software package ChemBioDraw Ultra version 11.0.2 running under Windows Vista in a conventional PC. They are (as mentioned above):

N'-((6-chloropyridin-3-yl)methyl)-N'-ethyl-N-methyl-2-nitroethene-1,1-diamine {nico1}; N-(1-((6-chloropyridin-3-yl)methyl)imidazolidin-2-ylidene)nitramide {nico2}; N-(3-((6-chloropyridin-3-yl)methyl)-5-methyl-1,3,5-oxadiazinan-4-ylidene)nitramide {nico3}; 1-((6-chloropyridin-3-yl)methyl)-3-methyl-2-nitroguanidine {nico4}; N-((6-chloropyridin-3-yl)methyl)-N'-cyano-N-methylacetimidamide {nico5}; N-(3-((6-chloropyridin-3-yl)methyl)thiazolidin-2-ylidene)cyanamide {nico6}; N'-ethyl-N-methyl-2-nitro-N'-(2-chlorothiazol-5-ylmethyl)ethene-1,1-diamine {nico7}; N-(1-((2-chlorothiazol-5-yl)methyl)imidazolidin-2-ylidene)nitramide {nico8}; N-(3-((2-chlorothiazol-5-yl)methyl)-5-methyl-1,3,5-oxadiazinan-4-ylidene)nitramide; {nico9} 1-((2-chlorothiazol-5-yl)methyl)-3-methyl-2-nitroguanidine {nico10}; N-((2-chlorothiazol-5-yl)methyl)-N'-cyano-N-methylacetimidamide {nico11}; N-(3-((2-chlorothiazol-5-yl)methyl)thiazolidin-2-ylidene)cyanamide {nico12}; N-(1-((tetrahydrofuran-3-yl)methyl)imidazolidin-2-ylidene) nitramide {nico13}; N-(3-methyl-5-((tetrahydrofuran-3-yl)methyl)-1,3,5-oxadiazinan-4-ylidene)nitramide {nico14}; 1-methyl-2-nitro-3-((tetrahydrofuran-3-yl)methyl)guanidine; N'-cyano-N-methyl-N-((tetrahydrofuran-3-yl)methyl) acetimidamide; N-(3-((tetrahydrofuran-3-yl)methyl)thiazolidin-2-ylidene)cyanamide {nico15}; 1-methyl-2-nitro-3-((tetrahydrofuran-3-yl)methyl)guanidine {nico16}

In the same way, and attending the same nomenclature followed above, we disclose the following compounds as preferred halogen substituted neonicotinoid insecticides:

N'-((6-fluoropyridin-3-yl)methyl)-N'-ethyl-N-methyl-2-nitroethene-1,1-diamine {nico17}; N-(1-((6-fluoropyridin-3-yl)methyl)imidazolidin-2-ylidene)nitramide {nico18}; N-(3-((6-fluoropyridin-3-yl)methyl)-5-methyl-1,3,5-oxadiazinan-4-ylidene)nitramide {nico19}; 1-((6-fluoropyridin-3-yl)methyl)-3-methyl-2-nitroguanidine {nico20}; N-((6-fluoropyridin-3-yl)methyl)-N'-cyano-N-methylacetimidamide {nico21}; N-(3-((6-fluoropyridin-3-yl)methyl)thiazolidin-2-ylidene)cyanamide {nico22}; N'-ethyl-N-methyl-2-nitro-N'-(2-fluorothiazol-5-yl)methyl)ethene-1,1-diamine {nico23}; N-(1-((2-fluorothiazol-5-yl)methyl)imidazolidin-2-ylidene) nitramide {nico24}; N-(3-((2-fluorothiazol-5-yl)methyl)-5-methyl-1,3,5-oxadiazinan-4-ylidene)nitramide {nico25}; 1-((2-fluorothiazol-5-yl)methyl)-3-methyl-2-nitroguanidine {nico26}; N-((2-fluorothiazol-5-yl)methyl)-N'-cyano-N-methylacetimidamide {nico27}; N-(3-((2-fluorothiazol-5-yl)methyl)thiazolidin-2-ylidene)cyanamide {nico28}; N'-((6-bromopyridin-3-yl)methyl)-N'-ethyl-N-methyl-2-nitroethene-1,1-diamine {nico29}; N-(1-((6-bromopyridin-3-yl)methyl)imidazolidin-2-ylidene)nitramide {nico30}; N-(3-((6-bromopyridin-3-yl)methyl)-5-methyl-1,3,5-oxadiazinan-4-ylidene)nitramide {nico31}; 1-((6-bromopyridin-3-yl)methyl-3-methyl-2-nitroguanidine {nico32}; N-((6-bromopyridin-3-yl)methyl)-N'-cyano-N-methylacetimidamide {nico33}; N-(3-((6-bromopyridin-3-yl)methyl)thiazolidin-2-ylidene)cyanamide {nico34}; N'-ethyl-N-methyl-2-nitro-N'-(2-bromothiazol-5-ylmethyl) ethene-1,1-diamine {nico35}; N-(1-((2-bromothiazol-5-yl) methyl)imidazolidin-2-ylidene)nitramide {nico36}; N-(3-((2-bromothiazol-5-yl)methyl)-5-methyl-1,3,5-oxadiazinan-4-ylidene)nitramide {nico37}; 1-((2-bromothiazol-5-yl) methyl)-3-methyl-2-nitroguanidine {nico38}; N-((2-bromothiazol-5-yl)methyl-N'-cyano-N-methylacetimidamide {nico39}; N-(3-((2-bromothiazol-5-yl)methyl)thiazolidin-2-ylidene)cyanamide {nico40}; N'-((6-iodopyridin-3-yl)methyl)-N'-ethyl-N-methyl-2-nitroethene-1,1-diamine {nico41}; N-(1-((6-iodopyridin-3-yl)methyl)imidazolidin-2-ylidene)nitramide {nico42}; N-(3-((6-iodopyridin-3-yl)methyl)-5-methyl-1,3,5-oxadiazinan-4-ylidene)nitramide {nico43}; 1-((6-iodopyridin-3-yl)methyl)-3-methyl-2-nitroguanidine {nico44}; N-((6-iodopyridin-3-yl)methyl)-N'-cyano-N-methylacetimidamide {nico45}; N-(3-((6-iodopyridin-3-yl)methyl)thiazolidin-2-ylidene)cyanamide {nico46}; N'-ethyl-N-methyl-2-nitro-N'-(2-iodothiazol-5-ylmethyl)ethene-1,1-diamine {nico47}; N-(1-((2-iodothiazol-5-yl)methyl)imidazolidin-2-ylidene) nitramide {nico48}; N-(3-((2-iodothiazol-5-yl)methyl)-5-methyl-1,3,5-oxadiazinan-4-ylidene)nitramide {nico49}; 1-((2-iodothiazol-5-yl)methyl)-3-methyl-2-nitroguanidine {nico50}; N-((2-iodothiazol-5-yl)methyl)-N'-cyano-N-methylacetimidamide {nico51}; N-(3-((2-iodothiazol-5-yl)methyl)thiazolidin-2-ylidene)cyanamide {nico52}.

Preferred dihalogenated substituted neonicatinoids are:

N'-((4,6-dichloropyridin-3-yl)methyl)-N'-ethyl-N-methyl-2-nitroethene-1,1-diamine {nico53};

N'-((4,6-difluoropyridin-3-yl)methyl)-N'-ethyl-N-methyl-2-nitroethene-1,1-diamine {nico54};

N'-((4,6-dibromopyridin-3-yl)methyl)-N'-ethyl-N-methyl-2-nitroethene-1,1-diamine {nico55};

N'-((4,6-diiodopyridin-3-yl)methyl)-N'-ethyl-N-methyl-2-nitroethene-1,1-diamine {nico56};

N-(1-((4,6-dichloropyridin-3-yl)methyl)imidazolidin-2-ylidene)nitramide {nico57};

N-(1-((4,6-difluoropyridin-3-yl)methyl)imidazolidin-2-ylidene)nitramide {nico58};

N-(1-((4,6-dibromopyridin-3-yl)methyl)imidazolidin-2-ylidene)nitramide {nico59};

N-(1-((4,6-diiodopyridin-3-yl)methyl)imidazolidin-2-ylidene)nitramide {nico60};

N-((4,6-dichloropyridin-3-yl)methyl)-N'-cyano-N-methylacetimidamide {nico61};
N-((4,6-difluoropyridin-3-yl)methyl)-N'-cyano-N-methylacetimidamide {nico62};
N-((4,6-dibromopyridin-3-yl)methyl)-N'-cyano-N-methylacetimidamide {nico63};
N-((4,6-diiodopyridin-3-yl)methyl)-N'-cyano-N-methylacetimidamide {nico64};
N-(3-((4,6-dichloropyridin-3-yl)methyl)thiazolidin-2-ylidene)cyanamide {nico65};
N-(3-((4,6-difluoropyridin-3-yl)methyl)thiazolidin-2-ylidene)cyanamide {nico66};
N-(3-((4,6-dibromopyridin-3-yl)methyl)thiazolidin-2-ylidene)cyanamide {nico67};
N-(3-((4,6-diiodopyridin-3-yl)methyl)thiazolidin-2-ylidene)cyanamide {nico68};
N-(3-((2,5-dichlorothiazol-5-yl)methyl)-6-methyl-1,3,5-oxadiazinan-4-ylidene)nitramide {nico69};
N-(3-((2,5-difluorothiazol-5-yl)methyl)-5-methyl-1,3,5-oxadiazinan-4-ylidene)nitramide {nico70};
N-(3-((2,5-dibromothiazol-5-yl)methyl)-5-methyl-1,3,5-oxadiazinan-4-ylidene)nitramide {nico71};
N-(3-((2,5-diiodothiazol-5-yl)methyl)-5-methyl-1,3,5-oxadiazinan-4-ylidene)nitramide {nico72}.

Preferred di- or trihalogenomethyl substituted neonicotinoids are:
N-((6-chloropyridin-3-yl)methyl)-N'-cyano-N-trichloromethylacetimidamide {nico73};
N-((6-chloropyridin-3-yl)methyl)-N' cyano-N-trifluoromethylacetimidamide {nico74};
1-((2-chlorothiazol-5-yl)methyl)-3-trifluoromethyl-2-nitroguanidine {nico74};
N-(3-((tetrahydrofuran-3-yl)difluoromethyl)thiazolidin-2-ylidene)cyanamide {nico75}

Note that for the purpose of the present invention, the term “insecticide” is just a non-limiting feature, used since it is normal in the field of the invention. Any biological activity granted because of the capability of the referred compounds to bind to nAChR acetylcholine receptors (even if they are not present in the target animal) is to be extended to other animals, as a non-limiting example, mites, fleas, Acaricidae and Insecta orders in general. It is to be understood that if the binding to the nAChR receptors has a physiological effect, the binding to a similar receptor shall have a similar effect, in the absence of the proof on the contrary. While it is true that there are neonicotinoids selective for insects (and not so toxic for humans) they have as well certain toxicity for human acetylcholine metabolism. The reverse may also be true for certain neonicotinoids and therefore interesting for commercial purposes.

The disclosed neonicotinoids {nicoNN} have differential activities on insects and any of them may turn to be of interest even if with a lower activity, they have lower toxicological profile or different characteristics regarding absorption, excretion and influence (toxicity, bee disorientation) in the non-targeted species. While the commercial neonicotinoids have shown improved insecticidal activity over most of the disclosed neonicotinoids, some of the newly disclosed neonicotinoids show an activity that may turn to be of highly relevance when tested routinely for other insects (even other animal orders), effort that is common task for the entomologist.

The synthesis of the 75 disclosed neonicotinoids (a part of them already state of the art) is easily done by state of the art different syntheses methods already used for the commercial neonicotinoids and published in different patents and/or journals. Particularly useful are the syntheses of Thiamethoxam in EP 580533, Clothianidin in EP 376279, Thiacloprid in EP 235725, Dinetofuran in EP 649845, Acetamiprid in WO 91/04965, Nitenpyram EP 302389 and Imidacloprid in EP 192060. Using those synthetic pathways and the appropriate building block (e.g., difluoro substituted pyridine-3-yl moiety instead of 2-chloropyridin-3-yl, or trifluoromethyl substituted starting materials) is evident for the skilled in the art to synthesize these compounds. Note that the proposed syntheses are based on the two parts of the neonicotinoid (A and B), and evident modifications will result in the disclosed neonicotinoids, however, the yield may be in some cases low. With state of the art separation techniques (crystallization, HPLC, preparative HPLC, LC, column chromatography, etc.) pure neonicotinoids will be obtained.

The inventors claim those neonicotinoids disclosed above that are novel over the prior art.

Preferred Crystal Polymorphs

We have realized that for commercial neonicotinoids, there exist (at least) two different polymorphic forms. Even for those not yet described or known by us, we prefer the use of the most thermodynamically stable crystal form at room temperature, since it is obvious that it will present less problems of agglomeration. It is evident for the crystallographer to find those modifications and which is the most stable form. While this is much more important in water based systems—normally—, it may have its advantages in oil based systems. Of course, presence of mixtures of polymorphs—or even pure crystals not thermodynamically being the most stable forms at room temperature—, but with slow kinetics into transformation in the most stable form may be equally used, since our formulations work without agglomeration problems whichever the crystal form is (even amorphous forms). Of course, when searching for the best result for an unknown period of storage (e.g. 5 years), we prefer the most thermodynamically stable form at room temperature. The inventors have realized the existence of multiple patents of crystal molecules of pesticides that have, for the inventors, the obvious use of avoiding agglomeration If they are the most thermodynamically stable forms in the ranges of temperatures of production and/or storage. We do not refrain to make use of this obvious use. The use of preferred crystal polymorphs (those stable at room temperature) is also to be applied for combinations with non-neonicotinoid pesticides, as disclosed elsewhere in this document.

Formulation of Neonicotinoids

Traditional formulations of neonicotinoids have been suspension concentrates (based in water), spot-on, collars, water dispersable granules, dusts, powders, etc. In agriculture, oil dispersions of neonicotinoids are known but only exceptionally of commercial application due to relevant flocculation, bleeding, redispersion and reemulsification problems. This is shocking at the view of the enormous and growing market share of neonicotinoids (in particular Imidacloprid) in the insecticide segment. Obviously, there must be a reason for such status quo of the neonicotinoids oil dispersions. It is a very complex problem to obtain an stable OD formulation that is satisfactorily biologically effective, not only for neonicotinoids, but in the latter case, much more difficult due to the chemical structure of them, and flocculation tendency derived thereof.

One main purpose of the present invention regarding ODs is to prepare formulations of any neonicotinoids for improved physicochemical quality of the formulation, including the protection against degradation of the active ingredient(s), emulsion and storage stability properties while at least maintaining the biological activity of similar formulation types or state of the art (only one known by us) OD of neonicotinoid with commercial quality.

The present invention solves this problem by the use of certain restricted coformulants (ingredients, components of the formulation) in certain restricted ranges and with the certainly uncommon incorporation of a milled inorganic polycationic salt in order to overcome sedimentation and problems of redispersibility. Note that the skilled in the art would avoid the use of a salt when working in an oil dispersion, since the use of salts are appropriate, according prior art, only to water based dispersions, and the introduction of further solids is not a good choice without inventiveness.

In this OD field, overwhelmingly over other fields, the compositions cannot be considered as the sum of the activity of every component in particular: our compositions show, without doubt, a synergistic effect of the components. There exist no additive effects without the high risk of destroying the usability of the formulation. The evaluation of the effect of each ingredient considered in isolation with respect prior ODs with an incomplete matching formulation recipe is an absurd task, since the presence of exactly as low as 4 components as disclosed in the prior art, even at the same concentration, may be absolutely irrelevant with regard formulation stability if a further new component is added to the formulation and affecting the surfactant/dispersant system (leading to a formulation that precipitates in half an hour, for example). These effects are well known by the skilled in the art, and rarely the interchange of a type of surfactant (or even within the same type, a different degree of mols of ethoxylation if surpassing the limits allowed by each formulation) leaves the formulation unaffected. Therefore, for evaluation of a formulation, it is needed the consideration of all the components at the same time, and particularly in cases like this, where instability is a serious problem.

The closest prior art is represented by D1=WO2007/028517 (Bayer CropScience), wherein certain oil dispersions of neonicotinoids are disclosed. It shares partially the problem of formulating a OD of neonicotinoids with proper biological efficacy (although inherently the formulation must be stable, two inseparable and inherent problems common to many formulations that need to pass the cut of high standards as the FAO specifications for plant protection products, and the farmer "cut" regarding efficacy). The problem addressed by D1 is to increase the biological performance of neonicotinoid plant protection products, in particular ODs, against the white fly by means of the use of certain penetrants. The problem of physicochemical stability is not addressed, and there is no hint in D1 for the need or even the possibility to increase the formulation stability. The claimed penetrants of D1 are usual surface active ingredients in crop chemistry, but not disclosed before for their use in neonicotinoids in oil dispersion. The problem is solved in D1 by means of the use of certain alcohol polyalkoxylates and other coformulants in defined ranges (at least at the view of dependent claims and examples). The evident drawbacks of oil dispersion of suspension concentrates in oil (synonym of oil dispersions, ODs) are summarized by the fact that despite their theoretical outperformance over other formulation types (given by the particular properties of oil dispersions regarding absorbance by plant and insect cuticles and epidermis and rainfastness) still there is only one commercially successful neonicotinoid in the European market, precisely Confidor® Imidacloprid 200 g/L OD of Bayer.

Our claim 1 is novel with regard the prior art, and particularly over D1, —noteworthy, as well over the commercial Confidor® OD at the time of filing) since the combination of ingredients of our ODs is not explicitly disclosed in D1 or any other prior art document. In D1 there is no need—either disclosure—to use the oil soluble nonionic polymeric oil dispersant with a HLB of 4-6, or mixtures thereof, namely, those of claim 1 b of this invention. The use of surfactant with a HLB below 7 would not be considered seriously since these surface active ingredients would tend to form emulsions of water in oil, exactly the contrary of what an OD must do. We have surprisingly found that the use of such surface active ingredients have an effect on the long storage stability properties of the formulation without affecting the emulsion properties. Further, such effect is synergistic with the use of an inorganic polycationic salt. A lower quantity of such oil dispersant with HLB of 4-6 would make the formulation (e.g., when the active ingredient is at 20 wt.-%) to bleed in a prolonged storage and a higher quantity would affect the properties of the emulsion in water before application, by the formation of multiple emulsions W/O/W due to the effect of such "reversed" HLB dispersant. While some nonionic dispersants have also being sometimes been recommended for suspension concentrates, these recommendations are based in that the referred dispersants have no significant influence on the emulsification properties, and as such, there is no sense in reporting their HLB value. This is the case, for example of the Atlox PS2 used in D1 that has no reported HLB value (see "Catalog of surfactants and derivatives" of ICI Specialty Chemicals—later Uniquema-50-3E/AS 6076-191/July 1989/Printed in Holland). However, we make use of at least a non-ionic polymeric dispersant of HLB of 4-6 (contrary to the desired effect of making an oil in water emulsion that would be provided with HLB values over 7, namely contrary to what would be obvious). This is the case of, for example, the effect Atlox 4912 with a HLB of 5.5. By virtue of the limitation to HLB from 4-6 in claim 1 b., the use of such non-ionic dispersant type is novel over D1 even if we would not consider simultaneously all the features of our invention. Each of the features in claim 1 b. c. d. e. and f. create in combination a non previously disclosed combination, that has its demonstrable inventive level due to the improved properties over the prior art on oil dispersions of neonicotinoids, and obviously, because the selection of components and ranges as herein disclosed cannot be done without an inventive effort. It is notable that in R1 (as well as in many other prior oil dispersion disclosures) there is paid no attention to the needed HLB of the surfactants. While the problem of penetration is solved in this invention by the total surface activity of the formulation given by all its components (and not due only to one or some of the components), penetrants claimed in D1 include day to day surfactants in agrochemistry as is the case of the alcohol ethoxylates/propoxylates: we may make use of them for their surfactant properties, not because their penetrating properties In addition to this, the surfactant system we have invented works in several types of oils not only in vegetable oils as referred to in D1. Contrary to the selected vegetable oils of D1, we have found best results with the use of paraffinic oils. Worthy to note, oil dispersions for other pesticides must not necessarily be of use for neonicotinoids, since neonicotinoids have a very specific chemical characteristics (that in turn are the reason of their activity), in particular the existence of lone ion pairs, a highly negatively charged part of the molecule (in the cyano or nitro position) in one "side" position—to the difference, e.g., of the "central" position of the urea group(s) in sulfonylureas-, and electron withdrawing groups that affect directly to the problems of irreversible flocculation and bleeding much more than many of the rest of pesticides (as for example sulfonylureas or pyrethroids). It cannot be extended freely the teaching given by the existence of vague (very broad) compositions of oil dispersions for other pesticides to the case of neonicotinoids. As usual in the formulation field, slight changes in the formulation components or even percentages of the same components, create drastic results in the product. Therefore, the components of our ODs are quite restricted, as well as their percentages in such a way that provide excellent results in emulsion properties (e.g., particle size when emulsified in water at 5%), storage stability tests and biological activity, that in no case can be deduced from any combination of prior art documents. Noteworthy, the skilled in the art at the view of D1 would tend to increase to percentage of penetrators, namely, alcohol ethoxylates/propoxylates.

We solve the problem of biological efficacy by obtaining median particle sizes well below of the prior art (see examples and comparisons), below 2 μm and percentile 90 below 5 μm: such oil dispersions of neonicotinoids have been never accomplished up to the date, in between other things, because the prior art incentives the search in the direction of finding penetrants, therefore being our claim 16 novel and with an inventive level unexpectedly high (at the view of the reduced amount of traditional penetrants and biological results).

Further, the present invention shows excellent emulsification profile and reemulsification/redispersion when the product has been standing for a long period (e.g., 24-36 hours) already in the spray tank, situation fairly frequent to need a solution when the farmer is not able to spray the whole quantity and/or the whole surface before the night or the day-off comes. With regard this redispersion effect we have surprisingly found that the use of preferred non-ionic polymers and, even better, with inorganic polycationic salts, are able to solve this problem, of course, in the context of the presence of the other formulation components. It is not usual, lesser easy (since increases the costs of milling and the viscosity due to higher solid content) and much lesser predictable that inorganic polycationic salts, most preferably aluminium sulfate salts, could have this effect without affecting the quality of the oil dispersion. While the use of polyvalent cationic salts is usual for water suspension concentrates, this cannot be directly applied to a ODs, wherein the own salt is insoluble and must be milled and create undesired interactions with the other coformulants or even promote growing of neonicotinoid crystals. This does not happen when using the ODs according the present invention, and do not influence either the neonicotinoids or the other selected pesticides if combined.

Imidacloprid, Thiamethoxam, Thiachloprid, Nitenpyram, Acetamiprid, Clothianidin and Dinetofuran and other neonicotinoids as disclosed above—with nAChR binding ability—are successfully formulated in oil suspension according the present invention with the use of certain copolymeric anionic dispersants, inorganic polycationic salt, sorbitan derivatives, ionic surfactants, other non-ionic surfactants and inorganic polyvalent cationic salt dispersed in the oil. The formulations produced show excellent storage stability properties regarding physiochemical parameters, including stability of the neonicotinoid active ingredient, reduced bleeding, and complete redispersibility, and they are biologically effective.

The use of viscosity modifiers is optional, but strongly recommended when the active ingredient is over 4 g/L.

Under a general term as "Imidacloprid" (and the other neonicotonoids) it must be understood to be comprised all the isomeric [this refers to the position of the nitro groups in E or Z, for example]/stereoisomeric forms of such chemical structure, as well as any of the possible crystallization forms, as well as its salts (e.g., hydrochloric and/or hydrobromic salts).

DETAILED DESCRIPTION OF THE INVENTION

The formulations object of the present invention must overcame several targets simultaneously, in between other things, to obtain some formulations that comply with the high quality standards of the FAO/WHO for Plant Protection Products (without prejudice that other formulations may not comply with all such requirements is needed for a particular purpose).

The problem is to find easily redispersible ODs of neonicotinoids, wherein the active ingredient(s) are not degraded significantly, with decreased wet sieving residue (below 1%), and with excellent emulsification properties, while maintaining the biological activity.

The inventive pathway has been focused in:

- decrease the particle size to improve the emulsion properties to obtain highly homogeneous and stable solutions to spray
- decrease the particle size finding an appropriate surfactant system to improve the biological efficacy instead of the prior art way of increasing the content of penetrants (focused only in fatty alcohol ethoxylates/propoxylates).
- decrease the wet sieve residue (indirectly reflecting redispersibility) by means of using certain surfactant systems and even improved with the use of polyvalent cationic salts milled with the formulation Our formulations have in general the following characteristics:

- contain at least a neonicotinoid compound at 0.5-40 wt.-%
- has a median particle size when measured in emulsion in water with a Laser Diffraction Particle Mastersizer of less than 2 μm and a percentile 90 of less than 5 μm
- do not present bleeding over 1% In volume of the formulation when letting it rest at room temperature for 4 days
- do not present neither oil nor cream separation after 2 hours in the emulsification test (5% of formulation in water, in measuring cylinder of 100 mL).

The solution to the problems addressed has being found to be oil suspensions or oil dispersions (synonym) formulations characterized in that they contain, with regard total weight of the oil dispersion formulation:

a. At least a neonicotinoid, or mixtures thereof, at 0.5-40 wt.-% b. A mixture of nonionic polymeric oil dispersants made of polyethoxylated glycol ester of a (poly)hydroxylated fatty acid chain with 12-20 carbons at 0.5-8 wt.-% with a HLB of 4-6 and a copolymer of type A-B-A of fatty acid with a chain of 12-20 carbons at 0.5-5 wt.-% c. A mixture made of polyethoxylated fatty alcohol at 0.5-15 wt.-%, and/or polypropoxylated fatty alcohol at 1-25 wt.-%, with a HLB of 12-16 d. At least a polyethoxylated and/or polypropoxylated sorbitan derivative at 3-30 wt.-%, with a HLB of 12-16 e. An alkylbenzenesulfonate sodium or calcium salt, being the alkyl chain of 10-14 carbon atoms, at 3-19 wt.-% f. A di-, tri- or tetra-valent cationic salt at 0.001 to 3 wt.-% g. An oil phase selected from paraffinic, naphtha aromatic, vegetable, synthetically modified vegetable oils; and mixtures thereof, at 30-70 wt.-%.

h. Optionally, non-ionic, anionic or cationic surface active ingredients not mentioned in claim 1 b, antioxidants, UV- and sun-light protectors, antimicrobial agents, pH regulators, viscosity modifiers selected from aluminium magnesium silicates, magnesium silicates, aluminosilicates, clays, modified clays, smectite, modified smectite, and present preferably at 0.1-5 wt.-%, antifoam, colouring agents, markers for traceability of the origin of the product, wherein the sum of all such compounds is not higher than 7 wt.-%, wherein the presence of other surface active ingredients than those of b., c., d. and e. is up to a maximum of 5 wt.-%, preferably.

A preferred formulation contains (always referred to total weight-% of the oil dispersion):

a. At least a neonicotinoid selected from Imidacloprid, Thiamethoxam, Thiacloprid, Nitenpyram, Acetamiprid, Clothianidin, Dinetofuran at 5-35 wt.-%
b. A mixture of nonionic polymeric oil dispersants made of polyethoxylated glycol ester of a (poly)hydroxylated fatty acid chain with 12-20 carbons at 0.5-8 wt.-% with a HLB of 4-6 and a copolymer of type A-B-A of fatty acid with a chain of 12-20 carbons at 0.5-3 wt.-%
c. A mixture made of 15-25 mols polyethoxylated stearyl alcohol at 0.5-10 wt.-%, 15-25 mols polyethoxylated oleyl alcohol at 0.5-10 wt.-% and 10-20 mols polypropoxylated monostearyl ether at 1-15 wt.-%, with a HLB of 12-16
d. A mixture made of 15-25 mols polyethoxylated sorbitan trioleate or tristearate at 5-20 wt.-% and 20-50 mols polyethoxylated sorbitan hepta-9-octadecenoate at 2-20 wt.-%, with a HLB of 12-16
e. Calcium or sodium dodecylbenzenesulfonate at 3-19 wt.-%
f. A paraffinic or vegetable oil at 30-70 wt.-%
g. A modified smectite at 0.3-1.5 wt.-%
h. Aluminium sulphate in anhydrous, monohydrate or any hydrated state at 0.005 to 0.3 wt.-%
i. An organomodified smectite at 0.3-3 wt.-%.

The presence of the inorganic salt produces an pronounced effect, synergistic with the presence of compounds included in b. above (see comparative examples 13 to 16), a sulphate or chloride, or phosphate of aluminium, magnesium, manganese, zinc, iron, copper, nickel, boron, gallium, indium, or mixtures thereof, in dehydrated or any hydration state. Preferred salt is aluminium sulphate, an most preferably monohydrated.

The compounds in which the formulations work especially well are the neonicotinoids with Compounds (I) as stated above with formula A-(CH2)—B Preferred neonicotinoids are Imidacloprid, Thiamethoxam, Thiacloprid, Nitenpyram, Acetamiprid, Clothianidin, Dinetofuran, in any of their isomeric or stereoisomeric forms when present and in any of their crystallization forms, salts thereof; and any mixtures thereof. The formulation has been intensively tested for Imidacloprid. However, other neonicotinoids behave as Imidacloprid.

The invention is also appropriate to combine other additional biologically active ingredients with at least one neonicotinoid, wherein such additional biologically active ingredient is selected from the group: insecticide, aracnicide, raticide, herbicide, fungicide, plant growth regulator, insect growth regulator, antibiotic, vitamin, oligoelement, fertilizer.

Preferred combinations with neonicotinoids are the compounds: 2,4-D; 2,4-DB; Alpha-Cypermethrin; Amitrole; Benalaxyl; Bentazone; Beta-Cyfluthrin; Bromoxynil; Carbendazim; Chlorothalonil; Chlorpropham; Chlorpyrifos; Chlorpyrifos-methyl; Chlorotoluron; Cyfluthrin; Cypermethrin; Daminozide; Deltamethrin; Desmedipham; Dinocap; Diquat; Esfenvalerate; Ethofumesate; Fluoroxypyr; Flusilazole; Glyphosate; Imazalil; Ioxynil; Iprodione; Isoproturon; Lambda-Cyhalothrin; Linuron; Mancozeb; Maneb; MCPA; MCPB; Mecoprop-P; Metiram; Metsulfuron; Molinate; Pendimethalin; Phenmedipham; Propiconazole; Propineb; Propyzamide; Pyridate; Thiabendazole; Thifensulfuron; Thiophanate-methyl; Thiram; Triasulfuron; Warfarin; Ziram; Captan; Clodinafop; Clopyralid; Cyprodinil; Dichlorprop-P; Dimethoate; Dimethomorph; Diuron; Ethepon; Ethoprophos; Fenamiphos; Fipronil; Folpet; Formetanate; Fosetyl; Glufosinate; Metconazole; Methiocarb; Metribuzin; Oxamyl; Phosmet; Pirimicarb; Pirimiphos-methyl; Propamocarb; Pyrimethanil; Rimsulfuron; Tolclofos-methyl; Tolylfluanid; Tribenuron-methyl; Triclopyr; Trinexapac; Triticonazole; Abamectin; Avermectins; Aclonifen; Amidosulfuron; Benfluralin; Bensulfuron; Bifenox; Chloridazon; Clofentezine; Clomazone; Cymoxanil; Dicamba; Difenoconazole; Diflubenzuron; Diflufenican; Dodemorph; Epoxiconazole; Fenoxaprop-P; Fenpropidin; Fenpropimorph; Fonpyroximate; Fluazinam; Fludioxonil; Flutolanil; Fuberidazole; Imazaquin; Lenacil; Calcium phosphide; Magnesium phosphide; Mepiquat; Metamitron; Metazachlor; Nicosulfuron; Oxadiazon; Picloram; Prosulfocarb; Pyriproxyfen; Quinoclamine; Sodium 5-nitroguaiacolate; Sodium o-nitrophenolate; Sodium p-nitrophenolate; Sulcotrione; Tobuconazole; Tebufenpyrad; Tralkoxydim; Triadimenol; Bacillus thuringiensis; Beauveria bassiana; Cydia pomonella granuiosis virus; Lecanicillimu muscarium; Metarhizium anisopliae; Phlebiopsis gigantean; Pythium oligandrum; Streptomyces K61—Streptomyces griseoviridis; Trichoderma atroviride; Trichoderma harzianum Rifai; Trichoderma polysporum; Trichoderma aspellerum; Trichoderma gamsii; Verticillium albo-atrum; Ethylene; Gibberellic acid; Gibberellin; Pyrethrins; Acibenzolar-S-methyl-Benzothiadiazole; Ampelomyces quisqualis; Azimsulfuran; Azoxystrobin; Bacillus subtilis; Beflubutamid; Benthiavalicarb; Benzoic acid; Bifenazate; Boscalid; Carfentrazone-ethyl; Clothianidin; Coniothyrium minitans; Cyazofamid; Cyclanilide; Cyhalofop-butyl; Haloxyfop; Dimethenamid; Dimoxystrobin; Etoxazole; Ethoxysulfuron; Famoxadone; Fenamidone; Fenhexamid; Flazasulfuron; Florasulam; Flufenacet; Flumioxazin; Fluoxastrobin; Flupyrsulfuron methyl; Flurtamone; Foramsulfuron; Forchlorfenuron; Fosthiazate; Gliocladium catenulatum; Imazamox; Imazosulfuron; Indoxacarb; Iodosulfuron-methyl-sodium; Iprovalicarb; Isoxaflutole; Kresoxim-methyl; Laminarin; Mepanipyrim; Mesosulfuron; Mesotrione; Metalaxyl-M; Methoxyfenozide; Metrafenone; Milbemectin; Oxadiargyl; Oxasulfuron; Paecilomyces fumosoroseus; Paecilomyces lilacinus; Pethoxamid; Picolinafen; Picoxystrobin; Prohexadione-calcium; Propoxycarbazone; Prosulfuron; Prothioconazole; Pseudomonas chlororaphis; Pymetrozine; Pyraclostrobin; Pyraflufen-ethyl; Quinoxyfen; S-Metolachlor; Silthiofam; Spinosad; Spiroxamine; Spodoptera exigua nuclear polyhedrosis virus; Sulfosulfuron; Tepraloxydim; Trifloxystrobin; Tritosulfuron; Zoxamide; Bifenthrin; Etofenprox; Propaquizafop; Teflubenzuron; Tetraconazole; Triflusulfuron; Zeta-Cypermethrin; Chlormequat; Chlorsulfuron; Cyromazine; Dimethachlor; Diphenylamine; Lufenuron; Penconazole; Quizalofop-P; Triallate; Triazoxide Acequinocyl; Adoxophyes orana; Aminopyralid; Amisulbrom; Aureobasidium pullulans; Benalaxyl-M; Bispyribac sodium; Candida oleophila; Chlorantraniliprole; Chromafenozide; Cyflufenamid; Disodium phosphonate; Emamectin benzoate; FEN 560; Flonicamid; Flubendiamide; Fluopicolide; Gamma-cyhalothrin; Halosulfuron methyl; Helicoverpa armigera nucleopolyhedrovirus; Heptamaloxyglucan; Ipconazole; Mandipropamid; Metaflumizone; Meptyldinocap; Novaluron; Orthosulfamuron; Paecilomyces fumosoroseus; Penoxsuiam; Phosphane; Pinoxaden; Profoxydim; Proquinazid; Pseudomonas sp. Starin; Pseudozyma flocculosa; Pyridalyl; Pyroxsulam; Silver thiosulphate; Spinetoram; Spirodiclofen; Spiromesifen; Spirotetramat; Spodoptera littorals nucleopolyhedrovirus; Tembotrione; Thiencarbazone; Topramezone; Trichoderma atroviride; Valiphenal; Zucchini Yellow Mosaic Virus.

Preferred are the combinations of Imidacloprid with those abovementioned pesticides, combinations of Acetamiprid with those pesticides, combinations of Thiacloprid with those pesticides or combinations of Thiamethoxam with those pesticides.

The oil dispersions according the present invention may contain additionally suspended microcapsules enclosing neonicotinoids and/or other pesticides than neonicotinoids, as those abovementioned.

The formulations according this invention are very appropriate for its use as a method to kill insects in the fields or house and garden, as well as mites, fleas (e.g., in capilar lotion in pharmacy), spiders and/or ticks (application to animals) in agricultural, veterinary or medicinal applications.

Regarding the compounds used in the examples, they are widely distributed by a multitude of distributors, including active ingredient have not been addressed in the Source information.

The White Oil must be understood as any paraffinic oil, also known in commercial products by "Basisöl", Isopar®, Marcol®, Puccini® (wherein the DMSO extract content is below 3%), and many other known commercial compounds used as well as basic paraffinic oils in cosmetic formulations, with the proviso that they are, of course, excluded from any known risks of carcinogenicity.

The use of naphta solvents is possible but not recommended for toxicological profile reasons. In any case is recommended the use of naphthalene depleted fractions. We have found best results with paraffinic or vegetable or modified vegetable oils. The preferred modifications to vegetable oils are those that impart to them more stability or handling advantages (as decreased viscosity). Alkylated oils, saponified oils, transisomerized oils, epoxidized oils are to be taken in consideration when performing this invention as possible oils. However, we prefer the use of highly saturated vegetable oils (or derivatives thereof) since they provide stability to the formulation. We have observed that some "pure" vegetable oils, with moderate content of unsaturations, and worst, highly unsaturated, even in the presence of BHT, produce with time hydroperoxides and then free radicals that, in combination with UV- and/or sun-light lead to a faster degradation of the neonicotinoids. In general gums (as rosin gum) and the like shall be understood to fall into the concept vegetable oil. Note as well that paraffins are also noted sometimes as waxes, denomination that shall not affect the extent of protection.

The fact in that in the examples there are no mixtures of active ingredients is due to give a broad overview of the formulation, while maintaining a reasonable amount of data. The inventors have verified that the benefit of the claimed compositions are as well present for:

Mixtures of different oil types, specially mixtures of vegetable (and derivatives thereof) and paraffinic oils Mixtures of active ingredients within the group of neonicotinoids and neonicotinoids and other pesticides, preferable not in the form of salts Use of non preferred (not claimed in specific necessary features) surface active ingredients that amount not more than 5 wt.-%

Use of coformulants as needed for the formulation (antifoams, antioxidants, UV and sun-light protectors, fluorescent or other type of markers to trace the origin of the ware in the market, antimicrobial agents, pH regulators, viscosity modifiers, antifoam, coloring agents, provided that the use of non preferred surface active ingredients and/or these compounds is not higher than 7 wt.-%

Other combinations that are evident for the skilled in the art.

The skilled in the art shall immediately notice when a non-preferred surfactant (or a non-neonicotinoid pesticide) is not compatible with the formulation according our invention by the presence within 24 hours of precipitates in the finished formulation (that shall be according the invention an homogeneous fluid) or rapid decomposition (within 24 hours more than 2% of decomposition) of the active ingredient neonicotinoid. This is said without prejudice in that we have not found any compound that falls under this exception, and therefore the claim works in the whole claimed range, and of course with more security, at the view of the recommendation of the description.

An important aspect of the present invention is the possibility to combine the claimed OD with other suitable formulation types as Emulsion Concentrate, Emulsion in Water, Suspoemulsion, Suspension Concentrate (in water), and particularly with Capsule Suspensions. The general method for these combination was firstly published by the same inventors in EP 1844653-A1.

We refer specially for the combination of OD of neonicotinoids with any other pesticides present in other formulation types (or even as well in the form of OD whether as disclosed herein or in a prior art type, having into account that then, the total stability will decrease), but preferably, with those parasiticides (e.g., ectoparasites for animal and human health) or insecticides/acaricides that may overcome problems of resistance to neonicotinoids, in the fields of Agriculture, Pharmacy or Veterinary and Fisheries. Particularly interesting are the mixtures:

Imidacloprid+Spinosad, Imidacloprid+Abamectin, Imidacloprid+Methoprene, Imidacloprid Buprofezin, Imidacloprid+Azadirachtin, Imidacloprid+Cyromazine, Imidacloprid+Fenoxycarb, Imidacloprid+Lambda-Cyhalothrin, Imidacloprid+Gamma-Cyhalothrin, Imidacloprid+Acrinathrin, Imidacloprid+Allethrin, Imidacloprid+Alpha-Cypermethrin, Imidacloprid+Beta-Cyfluthrin, Imidacloprid+Beta-Cypermethrin, Imidacloprid+Bifenthrin, Imidacloprid+Bioallethrin, Imidacloprid+bioresmethrin, Imidacloprid+Cycloprothrin, Imidacloprid+Cyfluthrin, Imidacloprid+Cyhalothrin, Imidacloprid+Cypermethrin, Imidacloprid+Cyphenothrin, Imidacloprid+Deltamethrin, Imidacloprid+Empenthrin, Imidacloprid+Esfenvalerate, Imidacloprid+Fenpropathrin, Imidacloprid+Fenvalerate, Imidacloprid+Flucythrinate, Imidacloprid+Flumethrin, Imidacloprid+Imidaclopridprothrin, Imidacloprid+Methothrin, Imidacloprid+Permethrin, Imidacloprid+Phenothrin (1-R-trans), Imidacloprid+Prallethrin, Imidacloprid+Resmethrin, Imidacloprid+RU 15525, Imidacloprid+Tau-Fluvalinate, Imidacloprid+Tefluthrin, Imidacloprid+Tetramethrin (1-R), Theta-Cypermethrin, Imidacloprid+Tralomethrin, Imidacloprid+Transfluthrin, Imidacloprid+Zeta-Cypermethrin, Imidacloprid+ZXI 8901, Imidacloprid+Ethiprol, Imidacloprid+Fipronil, Imidacloprid+Bistrifluoron, Imidacloprid+Chlorfluaturon, Imidacloprid+Diflubenzuron, Imidacloprid+Flucycloxuron, Imidacloprid+Flufenoxuron, Imidacloprid+Hexaflumuron, Imidacloprid+Lufenuron, Imidacloprid+Novaluron, Imidacloprid+Noviflumuran, Imidacloprid+Teflubezuron, Imidacloprid+Triflumuron, Imidacloprid+SZI-121, Imidaclorpid+at least one microbial pesticide.

It is also disclosed herein explicitly all the mixtures abovementioned wherein Imidacloprid is substituted by Thiacloprid. This applies as well to Thiamethoxam, which mixtures with the abovementioned pesticides are fully disclosed. In the same way, all the above mixtures are herein disclosed in full with Dinetofuran instead Imidacloprid. Last, such full and explicit disclosure includes mixtures of Acetamiprid with the pesticides disclosed above as well as with Clotianidin. We avoid unnecessary repetition of the mixtures as disclosed and claimed.

It is as well disclosed ternary or quaternary mixtures of at least one neonicotinoid and at least one of the cited compounds parasiticides.

Of the mixtures cited for parasiticides, the preferred embodiments are ODs wherein the neonicotinoids (at least one) are suspended in the OD and the other parasiticides are enclosed in microcapsules, most preferably, polyurea or polyurea-glycoluril microcapsules (which can be obtained as best option according prior art EP 1840145-A1 (Casaña-Giner, V.; Gimeno M. and Gimeno B.). The combination of ODs with other suitable formulation types are disclosed in EP 1844653-A1 (Casaña-Giner, V.; Gimeno M. and Gimeno B.) Such microcapsules contain in the core preferably an oily phase (normal phase microcapsules) but they may contain as well a water phase with dispersed or dissolved parasiticides active ingredients (reverse phase microcapsules).

In making such mixtures, care must be taken with the use of Aluminium Sulfate or other used multivalent cationic salt, since values over 0.3 wt.-% may provoke flocculation of the microcapsules. However, as shown in the example, the benefit of such use in the OD is still beneficial and at the level of the example, is not prejudicial for the stability of the CX formulation (OD+CS).

EXAMPLES

For a better understanding of the Examples, the following table is provided for allowing the skilled in the art to find the many commercial options that correspond to the selected Components of the formulations, and to compare with the prior art. In no way, the following list is presented in a restrictive way, and any chemical class as claimed may be replaced by other commercial (or non-commercially made) compounds that belong to the same classes are clearly specified in the claims.

TABLE 1

| Component (Source) | Chemical Class | Category according Claim 1 |
|---|---|---|
| Imidacloprid | neonicotinoid | a. |
| Corn oil | vegetable oil phase | f. |
| sunflower oil | vegetable oil phase | f. |
| White oil | paraffinic oil phase | f. |
| Methylated coconut oil | synthetic vegetable oil phase | f. |
| Atlox 4894 (Uniquema) | non-ionic dispersant | h. |
| Atlox 4838B (Uniquema) | calcium dodecylbenzenesulfonate | e. |
| Atlox 4912 (Uniquema) | PEG polyhydroxystearic acid | b. |
| Atlox 4913 (Uniquema) | non-ionic dispersant | h. |
| Atlox M8A 13/20 (Uniquema) | non-ionic dispersant | h. |
| Atlox LP1 (Uniquema) | A-B-A copolymer of fatty acid | b. |
| Atlox P52 (Uniquema) | non-ionic dispersant | h. |
| Atlas G-1281 (Uniquema) | non-ionic dispersant | h. |
| Arlamol E (Uniquema) | POP monostearyl ether | c. |
| Arlatone T (Uniquema) | sorbitan derivative | d. |
| Genapol LA 050 (Clariant) | POE lauryl ether | c. |
| Brij 98 (Uniquema) | POE monooleyl ether | c. |
| Brij 721 (Uniquema) | POE monostearyl ether | c. |
| Tween 80 (Uniquema) | sorbitan derivative | d. |
| Tween 85 (Uniquema) | sorbitan derivative | d. |
| Borresperse NA (LignoTech) | lignosulfonate | h. |
| Emulsogen CAL (Clariant) | calcium dodecylbenzenesulfonate | e. |
| Bentone SD1 (Pointer&Rothsch.) | modified smectite | h. |
| Aluminium sulfate monohydrate | trivalent cationic salt | f. |
| BHT | antioxidant | h. |
| Escalol 509 (ISP) | light protection agent | h. |
| Germal II (ISP) | antimicrobian | h. |
| Trisiloxane polyether (Evonik) | antifoam/non-ionic surfactant | h. |
| Silicon 1132 (Wacker) | antifoam/non-ionic surfactant | h. |

TABLE 2a

| Content in wt.-% | [1]Ex. 1 | [2]Ex. 2 | [3]Ex. 3 | [4]Ex. 4 | [5]Ex. 5 | [6]Ex. 6 | [7]Ex. 7 | [8]Ex. 8 | [9]Ex. 9 |
|---|---|---|---|---|---|---|---|---|---|
| Imidacloprid | 18.3 | 19.6 | 19.6 | 32 | 23.1 | 21.9 | 20 | 30 | 20 |
| Corn oil | 42.75 | 0 | 0 | 0 | 0 | 0 | ? | 0 | 0 |
| Sunflower oil | 0 | 40.1 | 40.15 | 29.75 | 39.65 | 0 | ? | 30 | 35 |
| White oil | 0 | 0 | 0 | 0 | 0 | 44.2 | ? | 0 | 0 |
| Methylated coconut oil | 0 | 0 | 0 | 0 | 0 | 0 | ? | 0 | 0 |
| Atlox 4894 | 0 | 0 | 0 | 0 | 0 | 0 | ? | 0 | 0 |
| Atlox 4838B | 4.2 | 0 | 0 | 0 | 0 | 0 | ? | 0 | 0 |
| Atlox 4912 | 0 | 0 | 0 | 0 | 0 | 0.57 | NO | 0 | 0 |
| Atlox 4913 | 0 | 0 | 0 | 0 | 0 | 0 | ? | 0 | 0 |
| Atlox MBA 13/20 | 2.5 | 0 | 0 | 0 | 0 | 0 | ? | 0 | 5 |
| Atlox LP1 | 0 | 0 | 0 | 0 | 0 | 1.67 | NO | 0 | 0 |
| Atlox PS2 | 0 | 5 | 0 | 5 | 5 | 0 | ? | 25 | 5 |
| Atlas G-1281 | 0 | 0 | 5 | 0 | 0 | 0 | ? | 5 | 0 |
| Arlamol E | 0 | 0 | 0 | 0 | 0 | 0 | ? | 0 | 0 |
| Arlatone T | 10 | 10 | 10 | 10 | 10 | 0 | ? | 0 | 0 |

TABLE 2a-continued

| Content in wt.-% | [1]Ex. 1 | [2]Ex. 2 | [3]Ex. 3 | [4]Ex. 4 | [5]Ex. 5 | [6]Ex. 6 | [7]Ex. 7 | [8]Ex. 8 | [9]Ex. 9 |
|---|---|---|---|---|---|---|---|---|---|
| Genapol LA 050 | 20 | 20 | 20 | 20 | 20 | 0 | ? | 5 | 35 |
| Brij 98 | 0 | 0 | 0 | 0 | 0 | 0 | ? | 0 | 0 |
| Brij 721 | 0 | 0 | 0 | 0 | 0 | 7 | ? | 0 | 0 |
| Tween 80 | 0 | 0 | 0 | 0 | 0 | 0 | ? | 0 | 0 |
| Tween 85 | 0 | 0 | 0 | 0 | 0 | 0 | ? | 0 | 0 |
| Borresperse NA | 2 | 5 | 5 | 3 | 2 | 0 | ? | 5 | 0 |
| Calsogen AR 100 ND | 0 | 0 | 0 | 0 | 0 | 7 | ? | 0 | 0 |
| Bentone SD1 | 0 | 0 | 0 | 0 | 0 | 3.08 | ? | 0 | 0 |
| Aluminium sulfate | 0 | 0 | 0 | 0 | 0 | 0 | NO | 0 | 0 |
| BHT (Bayer) | 0.2 | 0.2 | 0.2 | 0.2 | 0.2 | 0 | ? | 0 | 0 |
| Escalol 509 (ISP) | 0 | 0 | 0 | 0 | 0 | 0 | ? | 0 | 0 |
| Germal II | 0 | 0 | 0 | 0 | 0 | 0 | ? | 0 | 0 |
| Trisiloxane polyether | 0 | 0 | 0 | 0 | 0 | 14.2 | ? | 0 | 0 |
| Silicon 1132 | 0.05 | 0.1 | 0.05 | 0.05 | 0.05 | 0.38 | ? | 0 | 0 |

TABLE 2b

| Content in wt.-% | [10]Ex. 10 | Ex. 11 | Ex. 12 | Ex. 13 | Ex. 14 | Ex. 15 | Ex. 16 | Ex. 17 | Ex. 18 |
|---|---|---|---|---|---|---|---|---|---|
| Imidacloprid | 20.6 | 18.3 | 27 | 21.8 | 21.8 | 21.8 | 21.8 | 20 | 20.67 |
| Corn oil | 0 | 0 | 0 | 0 | 0 | 0 | 0 | 0 | 0 |
| Sunflower oil | 0 | 0 | 0 | 0 | 0 | 0 | 0 | 0 | 0 |
| White oil | 0 | 42.75 | 0 | 48 | 48.15 | 49 | 48.15 | 40.69 | 0 |
| Methylated coconut oil | 43 | 0 | 43 | 0 | 0 | 0 | 0 | 0 | 46.68 |
| Atlox 4894 | 0 | 0 | 0 | 0 | 0 | 0 | 0 | 0 | 0 |
| Atlox 4838B | 0 | 0 | 0 | 0 | 0 | 0 | 0 | 0 | 0 |
| Atlox 4912 | 4 | 4.2 | 3 | 2 | 2 | 0 | 0 | 5 | 2.1 |
| Atlox 4913 | 0 | 0 | 0 | 0 | 0 | 0 | 0 | 0 | 0 |
| Atlox MBA 13/20 | 0 | 0 | 0 | 0 | 0 | 0 | 0 | 0 | 0 |
| Atlox LP1 | 2 | 2.5 | 3 | 2 | 2 | 0 | 0 | 5 | 3.4 |
| Atlox PS2 | 0 | 0 | 0 | 0 | 0 | 0 | 0 | 0 | 0 |
| Atlas G-1281 | 0 | 0 | 0 | 0 | 0 | 0 | 0 | 0 | 0 |
| Arlamol E | 1 | 3 | 4 | 3 | 3 | 3 | 3 | 0 | 2 |
| Arlatone T | 1 | 3 | 0 | 2 | 2 | 2 | 2 | 9 | 2 |
| Genapol LA 050 | 1.9 | 3 | 2 | 0 | 0 | 3 | 4 | 19 | 0 |
| Brij 98 | 1 | 1 | 0 | 0.4 | 0.4 | 0.4 | 0.4 | 0 | 1 |
| Brij 721 | 1 | 1 | 0 | 0.4 | 0.4 | 0.4 | 0.4 | 0 | 1 |
| Tween 80 | 10 | 4 | 7.4 | 8 | 8 | 8 | 8 | 0 | 0 |
| Tween 85 | 0 | 12.9 | 0 | 0 | 0 | 0 | 0 | 0 | 9 |
| Borresperse NA | 0 | 0 | 0 | 0 | 0 | 0 | 0 | 0 | 0 |
| Calsogen AR 100 ND | 6 | 4 | 10 | 12 | 12 | 12 | 12 | 0 | 11 |
| Bentone SD1 | 1 | 0.2 | 0 | 0.2 | 0.2 | 0.2 | 0.2 | 0 | 1 |
| Aluminium sulfate | 0.09 | 0.1 | 0.2 | 0.15 | 0 | 0.15 | 0 | 0.1 | 0.15 |
| BHT | 0.1 | 0 | 0.35 | 0 | 0 | 0 | 0 | 0.2 | 0 |
| Escalol 509 | 0.09 | 0 | 0 | 0 | 0 | 0 | 0 | 1 | 0 |
| Germal II | 0.02 | 0 | 0 | 0 | 0 | 0 | 0 | 0 | 0 |
| Trisiloxane polyether | 7.2 | 0 | 0 | 0 | 0 | 0 | 0 | 0 | 0 |
| Silicon 1132 | 0 | 0.05 | 0.05 | 0.05 | 0.05 | 0.05 | 0.05 | 0.01 | 0 |

Explicative Notes of Table 2a and Table 2b:

1Ex. 1 is Ex. 1 of WO 07/028,517, outside of scope of the present invention; 2Ex. 2 is Ex. 2 of WO 07/028,517, outside of scope of the present invention; 3Ex. 3 is Ex. 3 of WO 07/028,517, outside of scope of the present invention; 4Ex. 4 is Ex. 4 of WO 07/028,517, outside of scope of the present invention; 5Ex. 5 is Ex. 5 of WO 07/028,517, outside of scope of the present invention; 6Ex. 6 is Ex. A of Table 1 of WO 08/155,108, outside of scope of the present invention; 7Ex. 7 is a commercial formulation of Confidor OD 200 g/L Imidacloprid, outside of scope of the present invention, and present in the Greek market in 2008 as recently produced product—while the components are known to us by analysis, they are not presented here, since for the purposes of the description only the lack of some of the components is relevant—; 8Ex. 8 is falling on the scope of claims 1, 2 and 3 of WO 07/028,517 (namely, restricted and preferred ranges of that invention), outside of scope of the present invention.

Results regarding physicochemical properties and biological efficacy.

Photostability of the active ingredient.

Ex. 1, Ex. 10, Ex. 13, Ex. 16 and Ex. 18 were exposed to natural sunlight in opened to the air metallic infrared weight plates (0.7 cm high load) during one week. After that period, Ex. 10 showed the least decomposition of Imidacloprid. Ex. 1 showed 45% more decomposition than Ex. 10. Ex. 13 showed only 7% more decomposition than Ex. 10, while Ex. 16 showed increase of 23% decomposition with regard Ex. 10. Ex. 18 showed 14% more decomposition than Ex. 10. Results are expressed in relative percentages for easiness of reproduction of the assay.

This shows that the formulation according the invention when containing a highly saturated vegetable oil (methylated coconut oil) with the UV-protector Escalol® 509, shows the least photodegradation of Imidacloprid. Ex. 1, being a vegetable oil present seems to be affected by light and oxygen, probably due to induced free radical oxidation of unsaturated fatty acids of the corn oil exposed to light (and not protected enough with the use of BHT). It is not specially surprising that the use of Escalol® increases the stability of Imidacloprid, but it is surprising at the view of prior art, since up to the date the inventors do not known any proposal to use UV-protectants for neonicotinoids in OD formulations. Namely, the prior art seems not to be aware of this problem. Ex. 16 showed better behavior (the tests were limited and did not allowed to extract absolute confidence intervals) than prior art Ex. 1, being surprising that the only difference with Ex. 13 (that had only 7% decomposition) is the presence of the crystal film-forming selected polymers Atlox® 4912 and Atlox® LP1. This may indicate (as the very clear results regarding stability of the formulation and bleeding) that indeed the neonicotinoids are effectively covered by such films even in the oily state. It is noteworthy that the oil in Ex. 13, 16 and 18 is a paraffinic oil, much less prone to photooxidation than the prior art vegetable oils. While the extent of the test is not enough detailed to discriminate in between the many factors that may have affected the results, we can only say that the rests of the components present in the invention may be as well the reason for such result, and as such we can only claim the formulation as a whole in order to be consistent with the results. It is unknown the real environment of the Imidacloprid crystals in a formulation of 10 to 17 components. However, according to the invention, it is observed some effect on protection of Imidacloprid when exposed to sunlight and air (what happens after spraying the product in the field).

It is proposed that the stability of Imidacloprid (and supposedly all neonicotinoids) follows the order in paraffinic oil>in vegetable oil. For equal coformulants, the presence of lipophilic non-ionic of the type claim 2 b could provide certain UV or visible light protection.

Thanks to the comparison of Ex. 13, 14, 15 and 16, it is clear that the use of the preferred non-ionic surfactants as claimed improve the stability of the formulation over prior art, and the use of polyvalent cationic salts are even more beneficial, showing a synergistic effect.

Effect on particle size.

The inventors, to the difference of the closest prior art, have taken the approach to reduce to the maximum the particle size, while having excellent physicochemical properties, of the OD, in order to increase the biological activity. While the skilled in the art would surely try to look for penetrants for the cuticle, maximum after the clear teaching of previous Bayer's patents on neonicotinoids ODs, we have taken a much more complicated approach. To reduce the particle size increases the risk in that the molecules of neonicotinoid present in the emulsion pass to the water phase and crystallize irreversible. Further, the emulsification power may compromise the solubility of all the ingredients in order to achieve an homogeneous liquid in which all coformulants are dissolvent or properly dispersed in crystals. More surprisingly, the simplest way to reduce the particle size (if there is no care on later problems on stability) is to increase significantly the quantity of surfactants. Further, for this purpose, the presence of surfactants of the type Atlox 4912 would be avoided since this helps to form water in oil emulsions, introducing the risk of W/O/W double emulsions with corresponding higher particle size. It is therefore absolutely unexpected that the we got mean (and median) particle sizes even below 1 μm, and a percentile 90 of below 2 μm. Surprisingly, the size of the crystals is not the reason of such low particle size (obviously, the crystal size, influenced by the degree of milling, must be below of 2-4 μm, but prior art formulations with such crystal sizes show particle sizes rarely below a mean size of 15 μm, so the reason of our astonishing small particle size resides in the synergistic formulation). Care must be taken with this: here we refer to the value of the conventional laser diffraction particle sizers (as Mastersizer®), where it considers both crystals over 4 μm as well, but the contribution to total size is reduced by the amount of much more particles with lower diameter. This unexpected effect is proven by: the use of Atlox 4912 and Atlox LP1 that would produce precisely the contrary, the non-increase of total quantity of surfactants over prior art neonicotinoids ODs, the non-coalescence of very small particles and non-crystallization "out-of-the-tiny-drop" expected for such small particle size (the triazole fungicides, in between many pesticides, present such "going-out of the drop" effect, when the oil drop is so small). This combined with the fact that the biological effect is comparable (or even superior) to that achieved with the massive use of penetrating agents (normally 30% as shown in the examples of D1) as the prior art teaches, is without doubt unexpected. Again, in a such complex formulations we cannot without an extensive and extreme hard testing, isolate the activity of each ingredient with full certainty of its contribution to the particle size. Therefore we restrict the claimed formulations to those that share a complete surfactant system within reasonable limits. It is also proven by the inventors, whichever neonicotinoid is formulated, that the particle size won't depend on the active ingredient, due to their chemical similarity.

TABLE 3

| 1Particle size | Ex. 1 | Ex. 7 | Ex. 10 | Ex. 13 | Ex. 18 |
|---|---|---|---|---|---|
| D (v 0.5) [μm] | 15.7 | 18.4 | 0.9 | 0.4 | 0.5 |
| D (v 0.9) [μm] | 74.8 | 187.1 | 1.0 | 2.3 | 3.7 |

1Determined in Mastersizer™ Laser Diffraction equipment. Note that the measurement considers both the bigger crystals of Imidacloprid as well as the very small emulsified droplets. The shape of the peaks shows two maximums in all samples. Data given by the equipment considers all measured values.

It is astonishing the quite homogeneous and leptokurtic distribution of the formulations Ex. 10, 13 and 18 according to the present invention. The material is milled conventionally to have a final average crystal size of 75% of the crystals below 2 μm. Noteworthy, the crystals of Ex. 1 were milled to the same level, and microscopic observation of Ex. 7 (Confidor OD) shows a particle size below 2-5 μm as well (namely, the particle size of the emulsion droplets is not—only—due to the size of the crystals).

Effect on Biological Activity

The effects may be tested in canes 30×30×30 cm with reared approximately 500 Ceratitis capitata (Wiedemann) flies fed with protein yeast hydrolizate, males and females in ratio 1:1, 20 days old and spraying a 0.01% w/v emulsion of each Example (10 mL). After 2 hours letting all droplets to settle down and diminish aerial intoxication, 500 flies' lots must be transferred to the test cages. Time to die all flies (e.g., 15 minutes) is represented by Table 4:

TABLE 4

| | Ex. 1 | Ex. 7 | Ex. 10 | Ex. 13 | Ex. 18 |
|---|---|---|---|---|---|
| Time to die | 4h 45 min | 3h 15 min | 3h 45 min | 2h 15 min | 2h 45 min |

The time to penetrate the cuticle and kill the 500 flies of each cage is lower in Ex. 13 and Ex. 18, being Ex. 10 in an intermediate position in between Ex.1 and Ex. 7.

On the other hand, visual inspection of spreading of Imidacloprid formulations of the same examples an orange leaves showed that the Examples according the invention (10, 13 and 18) was more homogeneous and within a biggest area (deposition with Pasteur pipette 50 μL in spreaded leaves, visual inspection).

Therefore, not only the penetration to insect cuticle is even improved over prior art, but also the absorption onto leaves (at least for such insect and crop) is enhanced according our invention.

Effect on Physicochemical Stability

Here is where the invention acquires it maximum and distinguishable features over the prior art.

Results on the same samples as above are (all test according FAO/WHO Specifications for Plant Protection Products and CIPAC methods):

TABLE 5

|  | Ex. 1 | Ex. 7 | Ex. 10 | Ex. 13 | Ex. 14 | Ex. 18 |
|---|---|---|---|---|---|---|
| Particle size |  |  |  |  |  |  |
| D (v 0.5) [μm] | 15.7 | 18.4 | 0.9 | 0.8 | 0.6 | 0.5 |
| D (v 0.9) [μm] | 74.8 | 187.1 | 1.0 | 1.2 | 1.1 | 0.7 |
| Emulsion stability (5 mL of Formulation in 100 mL 342 ppm standard water) |  |  |  |  |  |  |
| 30 minutes | 0.5 mL cream | 2 mL cream | no cream | no cream | no cream | no cream |
| 2 hours | 3 mL cream/ 0.5 mL sediment/ [1]irreversible sedim. | 3 mL cream/ 0.2 mL sediment/ [2]reversible sedim. | no cream/ 0.1 mL sediment/ [3]reversible sedim. | no cream/ 0.3 mL sediment/ [4]reversible sedim. | no cream/ 0.3 mL sediment/ [5]reversible sedim. | no cream/ 0.2 mL sediment/ [6]reversible sedim. |
| 24 hours | 7 mL cream/ 1 mL sediment/ [7]irreversible sedim. | 4 mL cream/ 0.7 mL sediment/ [8]reversible sedim. | no cream/ 0.3 mL sediment/ [9]reversible sedim. | no cream/ 0.3 mL sediment/ [10]reversible sedim. | no cream/ 0.3 mL sediment/ [11]reversible sedim. | no cream/ 0.2 mL sediment/ [12]reversible sedim. |
| Bleeding (100 mL of Formulation in 100 mL cylinder) |  |  |  |  |  |  |
| 4 days | 25 mL oil on top | 15 mL oil on top | <1 mL on top | <1 mL on top | <1 mL on top | <1 mL on top |

[1]After 50 inversions of the measuring cylinder;
[2]25 inversions;
[3]10 inversions;
[4]11 inversions;
[5]19 inversions;
[6]9 inversions;
[7]50 inversions;
[8]45 inversions;
[9]23 inversions;
[10]23 inversions;
[11]33 inversions;
[12]19 inversions.

The results show that regarding bleeding, the formulations according the present invention are superior to the state of the art formulations. Further, the problem of sedimentation is solved according the present invention with approximately half of the energy with respect to comparative examples, that may suppose a crucial factor when the farmer tries to redisperse the sediment in the spray tank left filled or half-filled before continuing with the spray on the following day.

While not all the results are shown here, it has been observed that formulations Ex. 15 and Ex. 16 present irreversible sedimentation already after two hours. Moreover, consistently, redispersion was much improved when using aluminium sulfate in the formulation. The concomitant use of Atlox 4912 and LP1 plus aluminium sulfate clearly have consistently shown a lower energy for redispersion.

The wet sieve residue according the standardized test CIPAC MT 185 showed for all formulations according the invention a value below 0.1%.

Overview of all Tested Formulations

Herein are briefly reported short tests done on all Examples.

TABLE 6

|  | Emulsion (after 4 h) | Redispersibility (after 24 h) | Wet sieve residue (after storage 8 wk at 40° C.) | Bleeding in 100 mL (after 14 days at r.t.) |
|---|---|---|---|---|
| Ex. 1 | cream | yes | <0.1% | >5% |
| Ex. 2 | cream | yes | <0.1% | >5% |
| Ex. 3 | cream + oil | no | <0.1% | >5% |
| Ex. 4 | cream | yes | <0.1% | >5% |
| Ex. 5 | cream | yes | <0.1% | >5% |
| Ex. 6 | cream | no | <0.1% | >5% |
| Ex. 7 | cream | yes | <0.1% | >5% |

TABLE 6-continued

|  | Emulsion (after 4 h) | Redispersibility (after 24 h) | Wet sieve residue (after storage 8 wk at 40° C.) | Bleeding in 100 mL (after 14 days at r.t.) |
|---|---|---|---|---|
| Ex. 8 | cream | no | >0.5% | >10% |
| Ex. 9 | no cream/no oil | yes | <0.1% | <5% |
| Ex. 10 | no cream/no oil | yes | <0.1% | <5% |
| Ex. 11 | no cream/no oil | yes | <0.1% | <5% |
| Ex. 12 | no cream/no oil | yes | <0.1% | <5% |
| Ex. 13 | no cream/no oil | yes | <0.1% | <5% |
| Ex. 14 | no cream/no oil | no | <0.1% | <5% |
| Ex. 15 | no cream/no oil | no | >0.5% | >5% |
| Ex. 16 | no cream/no oil | no | >5% | >5% |
| Ex. 17 | no cream/no oil | yes | <0.1% | <5% |
| Ex. 18 | no cream/no oil | yes | <0.1% | <5% |

Example 19

Neonicotinoid OD with Pyrethroid CS formulation

A formulation of Imidacloprid OD according the invention was performed, and a Capsule Suspension (CS) formulation was performed as well, separately. Emulsification of one formulation into the other was performed as final step obtaining a fully functional OD-CS formulation (that we designate as CX formulation, in the absence of still an international code for this innovative formulation type). The procedure to create the CS formulation follow the teaching of the invention of the same authors and applicant EP 1840145-A1. The combination of CS formulations and OD formulations follow the teaching of the invention of the same authors and applicant EP 1844553-A1. A suitable OD+CS formulation, namely, a CX formulation is obtained with the following formula:

| | |
|---|---|
| Imidacloprid OD | |
| Atlox 4912 | 1.955 |
| Atlox LP1 | 1.169 |
| White oil | 56.636 |
| Brij 98V | 0.342 |
| Brij 721 | 0.342 |
| Arlamol E | 1.368 |
| Arlatone T | 1.368 |
| Tween 85 | 6.130 |
| Calsogen ARL 100 ND | 15.270 |
| Bentone SD 1 | 0.570 |
| Aluminiumsulfate-1-hydrate | 0.086 |
| Imidacloprid techical | 11.782 |
| Lambda-Cyhalothrin CS | |
| Water | 1.419 |
| $Na_2HPO_4$ | 0.027 |
| Synperonic ® PE/L 64 | 0.029 |
| Acrylic polymer with PVA | 0.017 |
| Xantan gum | 0.028 |
| Reax ® 88A | 0.046 |
| TEGO ® Antifoam MR138 | 0.003 |
| Citric Acid | 0.001 |
| Atlox 4913 | 0.043 |
| p-octylbenzenesulfonic acid | 0.004 |
| Gamma-Butyrolactone | 0.495 |
| Lambda Cyhalothrin technical | 0.740 |
| Ascorbyl palmitate | 0.003 |
| Formic acid | 0.001 |
| Tetramethoxymethyl glycoluril | 0.004 |
| TMXDI | 0.057 |
| PAPI | 0.043 |
| Dibutyltindilaurate | 0.004 |
| TEGO ® Antifoam MR 1015 | 0.003 |
| Keltrol ® | 0.002 |
| Pangel ® | 0.017 |
| SUM | 100.00 |

This formula shows a good control of trips and whitefly in greenhouse. Its functionality against many other pests is also ensured.

Example 20

Example 19 was repeated but using Deltamethrin instead of Lambda-Cyhalothrin. It shows a decrease of dermal toxicity of Deltamethrin when applied for the control of fleas in cats and dogs. It is therefore expected that the control of fleas In humans is as well improved over the prior art with the use of such formulation, when diluted to the usual concentration and mixed with conventional cosmetic ingredients state of the art for hair prevention and treatment of flea infestations.

Example 21

Replacing Deltamethrin by benzoylureas (as Lufenuron, proven as effective ovicide in Casaña-Giner et al., J. Econ. Entomol. (1999) Vol. 92(2), pp. 303-308), would increase notably the antiflea effect by virtue of long lasting biological effect added to the controlled release of microcapsules.

The invention claimed is:

1. An oil dispersion comprising, with regard to total weight of the oil dispersion formulation:

a. At least a neonicotinoid, or mixtures thereof, at 0.5-40 wt.-%;

b. A mixture of nonionic polymeric oil dispersants made of polyethoxylated glycol ester of a (poly)hydroxylated fatty acid chain with 12-20 carbons at 0.5-8 wt.-% with a HLB of 4-6 and a copolymer of type A-B-A of fatty acid with a chain of 12-20 carbons at 0.5-5 wt.-%;

c. A mixture comprising polyethoxylated fatty alcohol at 0.5-15 wt.-%, and/or polypropoxylated fatty alcohol at 1-25 wt.-%, with a HLB of 12-16;

d. At least a polyethoxylated and/or polypropoxylated sorbitan derivative at 3-30 wt.-%, with a HLB of 12-16;

e. An alkylbenzenesulfonate sodium or calcium salt, being the alkyl chain of 10-14 carbon atoms, at 3-19 wt.-%;

f. A di-, tri- or tetra-valent cationic salt at 0.001 to 3 wt.-%;

g. An oil phase selected from the group consisting of paraffinic, naphtha aromatic, vegetable, synthetically modified vegetable oils and mixtures thereof, at 30-70 wt.-%; and h. Optionally, coformulates selected from the group consisting of non-ionic, anionic or cationic surface active ingredients, antioxidants, UV- and sun-light protectors, antimicrobial agents, pH regulators, viscosity modifiers, aluminium magnesium silicates, magnesium silicates, aluminosilicates, clays, modified clays, smectites, modified smectites, antifoam, colouring agents, and markers for traceability of the origin of the product.

2. The oil dispersion according claim 1, further comprising coformulants selected from the group consisting of other non-ionic, anionic or cationic surface active ingredients, antioxidants, UV- and sun-light protectors, antimicrobial agents, pH regulators, viscosity modifiers selected from aluminium magnesium silicates, magnesium silicates, aluminosilicates, clays, modified clays, smectite, modified smectite, antifoam, colouring agents, and markers for traceability of the origin of the product.

3. The oil dispersion according to claim 1, wherein the di-, tri- or tetra-valent cationic salt is a sulphate or chloride, or phosphate of aluminium, magnesium, manganese, zinc, iron, copper, nickel, boron, gallium, indium, or mixtures thereof, in dehydrated or any hydration state.

4. The oil dispersion according to claim 1, wherein the neonicotinoid is selected from Compounds (I) of formula:

A-(CH2)—B    Compounds (I)

wherein A is selected from

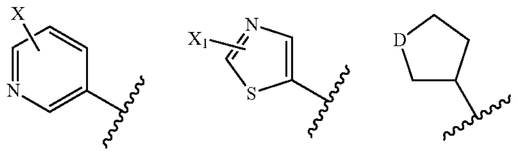

wherein X1 is selected from the halogens: chlorine, iodine, fluor, bromine; the halogen being attached to the heterocycle in any position except to the carbon atom that is bound to the (CH2) of compounds (I)—indicated by the curved line, as for B—and except to the heteroatom(s); and wherein up to two additional halogen atoms X2 and X3 are attached to the heterocycle in any of the resulting free positions;

and B is selected from

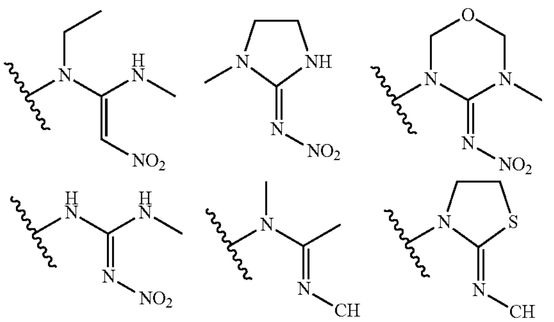

wherein the nitro or cyano group is in any isomeric position, being shown just one of the two isomeric positions for nitro or cyano, and wherein the methyl groups may be replaced by trifluoromethyl groups.

5. The oil dispersion according to claim 4 wherein the neonicotinoid is selected from the group consisting of: Imidacloprid, Thiamethoxam, Thiacloprid, Nitenpyram, Acetamiprid, Clothianidin, Dinetofuran, in any of their isomeric or stereoisomeric forms when present and in any of their crystallization forms, salts thereof; and any mixtures thereof.

6. The oil dispersion according to claim 1 comprising, referred to total weight percent of the oil dispersion formulation:

a. At least a neonicotinoid selected from Imidacloprid, Thiamethoxam, Thiacloprid, Nitenpyram, Acetamiprid, Clothianidin, Dinetofuran at 5-35 wt.-%;

b. A mixture of nonionic polymeric oil dispersants made of polyethoxylated glycol ester of a (poly) hydroxylated fatty acid chain with 12-20 carbons at 0.5-8 wt.-% with a HLB of 4-6 and a copolymer of type A-B-A of fatty acid with a chain of 12-20 carbons at 0.5-3 wt.-%;

c. A mixture made of 15-25 mols polyethoxylated stearyl alcohol at 0.5-10 wt.-%, 15-25 mols polyethoxylated oleyl alcohol at 0.5-10 wt.-% and 10-20 mols polypropoxylated monostearyl ether at 1-15 wt.-%, with a HLB of 12-16;

d. A mixture made of 15-25 mols polyethoxylated sorbitan trioleate or tristearate at 5-20 wt.-% and 20-50 mols polyethoxylated sorbitan hepta-9-octadecenoate at 2-20 wt.-%, with a HLB of 12-16;

e. Calcium or sodium dodecylbenzenesulfonate at 8-19 wt.-%;

f. A paraffinic or vegetable oil at 30-70 wt.-%;

g. Aluminium sulfate in anhydrous, monohydrate or any hydrated state at 0.005 to 0.3 wt.-%; and i. An organomodified smectite at 0.3-3 wt.-%.

7. The oil dispersion according to claim 1 or claim 6 further comprising an additional biologically active ingredient appropriate for combination with at least one neonicotinoid, wherein said additional biologically active ingredient is selected from the group consisting of: insecticide, aracnicide, raticide, herbicide, fungicide, plant growth regulator, insect growth regulator, antibiotic, vitamin, oligoelement, and fertilizer.

8. The oil dispersion according to claim 1 or claim 6 further comprising at least one additional suspended, dispersed, solubilized, microencapsulated and/or emulsified pesticide(s) selected from the group consisting of: 2,4-D; 2,4-DB; Alpha-Cypermethrin; Amitrole; Benalaxyl; Bentazone; Beta-Cyfluthrin; Bromoxynil; Carbendazim; Chlorothalonil; Chlorpropham; Chlorpyrifos; Chlorpyrifos-methyl; Chlorotoluron; Cyfluthrin; Cypermethrin; Daminozide; Deltamethrin; Desmedipham; Dinocap; Diquat; Esfenvalerate; Ethofumesate; Fluroxypyr; Flusilazole; Glyphosate; Imazalil; Ioxynil; Iprodione; Isoproturon; Lambda-Cyhalothrin; Linuron; Mancozeb; Maneb; MCPA; MCPB; Mecoprop-P; Metiram; Metsulfuron; Molinate; Pendimethalin; Phenmedipham; Propiconazole; Propineb; Propyzamide; Pyridate; Thiabendazole; Thifensulfuron; Thiophanate-methyl; Thiram; Triasulfuron; Warfarin; Ziram; Captan; Clodinafop; Clopyralid; Cyprodinil; Dichlorprop-P; Dimethoate; Dimethomorph; Diuron; Ethepon; Ethoprophos; Fenamiphos; Fipronil; Folpet; Formetanate; Fosetyl; Glufosinate; Metconazole; Methiocarb; Metribuzin; Oxamyl; Phosmet; Pirimicarb; Pirimiphos-methyl; Propamocarb; Pyrimethanil; Rimsulfuron; Tolclofos-methyl; Tolylfluanid; Tribenuron-methyl; Triclopyr; Trinexapac; Triticonazole; Abamectin; Avermectins; Aclonifen; Amidosulfuron; Benfluralin; Bensulfuron ; Bifenox; Chloridazon; Clofentezine; Clomazone; Cymoxanil; Dicamba; Difenoconazole; Diflubenzuron; Diflufenican; Dodemorph; Epoxiconazole; Fenoxaprop-P; Fenpropidin; Fenpropimorph; Fenpyroximate; Fluazinam; Fludioxonil; Flutolanil; Fuberidazole; Imazaquin; Lenacil; Calcium phosphide; Magnesium phosphide; Mepiquat; Metamitron; Metazachlor; Nicosulfuron; Oxadiazon; Picloram; Prosulfocarb; Pyriproxyfen; Quinoclamine; Sodium 5-nitroguaiacolate; Sodium o-nitrophenolate; Sodium p-nitrophenolate; Sulcotrione; Tebuconazole; Tebufenpyrad; Tralkoxydim; Triadimenol; Bacillus thuringiensis; Beauveria bassiana; Cydia pomonella granulosis virus; Lecanicillimu muscarium; Metarhizium anisopliae; Phlebiopsis gigantean; Pythium oligandrum; Streptomyces K61-Streptomyces griseoviridis; Trichoderma atroviride; Trichoderma harzianum Rifai; Trichoderma polysporum; Trichoderma aspellerum; Trichoderma gamsii; Verticillium albo-atrum; Ethylene; Gibberellic acid; Gibberellin; Pyrethrins; Acibenzolar-S-methyl-Benzothiadiazole; Ampelomyces quisqualis; Azimsulfuron; Azoxystrobin; Bacillus subtilis; Beflubutamid; Benthiavalicarb; Benzoic acid; Bifenazate; Boscalid; Carfentrazone-ethyl; Clothianidin; Coniothyrium minitans; Cyazofamid; Cyclanilide; Cyhalofop-butyl; Haloxyfop; Dimethenamid; Dimoxystrobin; Etoxazole; Ethoxysulfuron; Famoxadone; Fenamidone; Fenhexamid; Flazasulfuron; Florasulam; Flufenacet; Flumioxazin; Fluoxastrobin; Flupyrsulfuron methyl; Flurtamone; Foramsulfuron; Forchlorfenuron; Fosthiazate; Gliocladium catenulatum; Imazamox; Imazosulfuron; Indoxacarb; Iodosulfuron-methyl-sodium; Iprovalicarb; Isoxaflutole; Kresoxim-methyl; Laminarin; Mepanipyrim; Mesosulfuron; Mesotrione; Metalaxyl-M; Methoxyfenozide; Metrafenone; Milbemectin; Oxadiargyl; Oxasulfuron; Paecilomyces fumosoroseus; Paecilomyces lilacinus; Pethoxamid; Picolinafen; Picoxystrobin; Prohexadione-calcium; Propoxycarbazone; Prosulfuron; Prothioconazole; Pseudomonas chlororaphis; Pymetrozine; Pyraclostrobin; Pyraflufen-ethyl; Quinoxyfen; S-Metolachlor; Silthiofam; Spinosad; Spiroxamine; Spodoptera exigua nuclear polyhedrosis virus; Sulfosulfuron; Tepraloxydim; Trifloxystrobin; Tritosulfuron; Zoxamide; Bifenthrin;

Etofenprox; Propaquizafop; Teflubenzuron; Tetraconazole; Triflusulfuron; Zeta-Cypermethrin; Chlormequat; Chlorsulfuron; Cyromazine; Dimethachlor; Diphenylamine; Lufenuron; Penconazole; Quizalofop-P; Triallate; Triazoxide Acequinocyl; Adoxophyes orana; Aminopyralid; Amisulbrom; Aureobasidium pullulans; Benalaxyl-M; Bispyribac sodium; Candida oleophila; Chlorantraniliprole; Chromafenozide; Cyflufenamid; Disodium phosphonate; Emamectin benzoate; FEN 560; Flonicamid; Flubendiamide; Fluopicolide; Gamma-cyhalothrin; Halosulfuron methyl; Helicoverpa armigera nucleopolyhedrovirus; Heptamaloxyglucan; Ipconazole; Mandipropamid; Metaflumizone; Meptyldinocap; Novaluron; Orthosulfamuron; Paecilomyces fumosoroseus; Penoxsulam; Phosphane; Pinoxaden; Profoxydim; Proquinazid; *Pseudomonas* sp. Starin; Pseudozyma flocculosa; Pyridalyl; Pyroxsulam; Silver thiosulphate; Spinetoram; Spirodiclofen; Spiromesifen; Spirotetramat; Spodoptera littoralis nucleopolyhedrovirus; Tembotrione; Thiencarbazone; Topramezone; Trichoderma atroviride; Valiphenal; and Zucchini Yellow Mosaic Virus.

9. The oil dispersion according to claim 1 or claim 6 comprising as active ingredients Imidacloprid and one of the pesticides selected from the group consisting of: 2,4-D; 2,4-DB; Alpha-Cypermethrin; Amitrole; Benalaxyl; Bentazone; Beta-Cyfluthrin; Bromoxynil; Carbendazim; Chlorothalonil; Chlorpropham; Chlorpyrifos; Chlorpyrifos-methyl; Chlorotoluron; Cyfluthrin; Cvpermethrin; Daminozide; Deltamethrin; Desmedipham; Dinocap; Diquat; Esfenvalerate; Ethofumesate; Fluroxypyr; Flusilazole; Glyphosate; Imazalil; Ioxynil; Iprodione; Isoproturon; Lambda-Cyhalothrin; Linuron; Mancozeb; Maneb; MCPA; MCPB; Mecoprop-P; Metiram; Metsulfuron; Molinate; Pendimethalin; Phenmedipham; Propiconazole; Propineb; Propyzamide; Pyridate; Thiabendazole; Thifensulfuron; Thiophanate-methyl; Thiram; Triasulfuron; Warfarin; Ziram; Captan; Clodinafop; Clopyralid; Cyprodinil; Dichlorprop-P; Dimethoate; Dimethomorph; Diuron; Ethepon; Ethoprophos; Fenamiphos; Fipronil; Folpet; Formetanate; Fosetyl; Glufosinate; Metconazole; Methiocarb; Metribuzin; Oxamyl; Phosmet; Pirimicarb; Pirimiphos-methyl; Propamocarb; Pyrimethanil; Rimsulfuron; Tolclofos-methyl; Tolylfluanid; Tribenuron-methyl; Triclopyr; Trinexapac; Triticonazole; Abamectin; Avermectins; Aclonifen; Amidosulfuron; Benfluralin; Bensulfuron; Bifenox; Chloridazon; Clofentezine; Clomazone; Cymoxanil; Dicamba; Difenoconazole; Diflubenzuron; Diflufenican; Dodemorph; Epoxiconazole; Fenoxaprop-P; Fenpropidin; Fenpropimorph; Fenpyroximate; Fluazinam; Fludioxonil; Flutolanil; Fuberidazole; Imazaquin; Lenacil; Calcium phosphide; Magnesium phosphide; Mepiquat; Metamitron; Metazachlor; Nicosulfuron; Oxadiazon; Picloram; Prosulfocarb; Pyriproxyfen; Quinoclamine; Sodium 5-nitroguaiacolate; Sodium o-nitrophenolate; Sodium p-nitrophenolate; Sulcotrione; Tebuconazole; Tebufenpyrad; Tralkoxydim; Triadimenol; Bacillus thuringiensis; Beauveria bassiana; Cydia pomonella granulosis virus; Lecanicillimu muscarium; Metarhizium anisopliae; Phlebiopsis gigantean; Pythium oligandrum; Streptomyces K61-Streptomyces griseoviridis; Trichoderma atroviride; Trichoderma harzianum Rifai; Trichoderma polysporum; Trichoderma aspellerum; Trichoderma gamsii; Verticillium albo-atrum; Ethylene; Gibberellic acid; Gibberellin; Pyrethrins; Acibenzolar-S-methyl-Benzothiadiazole; Ampelomyces quisqualis; Azimsulfuron; Azoxystrobin; Bacillus subtilis; Beflubutamid; Benthiavalicarb; Benzoic acid; Bifenazate; Boscalid; Carfentrazone-ethyl; Clothianidin; Coniothyrium minitans; Cyazofamid; Cyclanilide; Cyhalofop-butyl; Haloxyfop; Dimethenamid; Dimoxystrobin; Etoxazole; Ethoxysulfuron; Famoxadone; Fenamidone; Fenhexamid; Flazasulfuron; Florasulam; Flufenacet; Flumioxazin; Fluoxastrobin; Flupyrsulfuron methyl; Flurtamone; Foramsulfuron; Forchlorfenuron; Fosthiazate; Gliocladium catenulatum; Imazamox; Imazosulfuron; Indoxacarb; Iodosulfuron-methyl-sodium; Iprovalicarb; Isoxaflutole; Kresoxim-methyl; Laminarin; Mepanipyrim; Mesosulfuron; Mesotrione; Metalaxyl-M; Methoxyfenozide; Metrafenone; Milbemectin; Oxadiargyl; Oxasulfuron; Paecilomyces fumosoroseus; Paecilomyces lilacinus; Pethoxamid; Picolinafen; Picoxystrobin; Prohexadione-calcium; Propoxycarbazone; Prosulfuron; Prothioconazole; Pseudomonas chlororaphis; Pymetrozine; Pyraclostrobin; Pyraflufen-ethyl; Quinoxyfen; S-Metolachlor; Silthiofam; Spinosad; Spiroxamine; Spodoptera exigua nuclear polyhedrosis virus; Sulfosulfuron; Tepraloxydim; Trifloxystrobin; Tritosulfuron; Zoxamide; Bifenthrin; Etofenprox; Propaquizafop; Teflubenzuron; Tetraconazole; Triflusulfuron; Zeta-Cypermethrin; Chlormequat; Chlorsulfuron; Cyromazine; Dimethachlor; Diphenylamine; Lufenuron; Penconazole; Quizalofop-P; Triallate; Triazoxide Acequinocyl; Adoxophyes orana; Aminopyralid; Amisulbrom; Aureobasidium pullulans; Benalaxyl-M; Bisplribac sodium; Candida oleophila; Chlorantraniliprole; Chromafenozide; Cyflufenamid; Disodium phosphonate; Emamectin benzoate; FEN 560; Flonicamid; Flubendiamide; Fluopicolide; Gamma-cyhalothrin; Halosulfuron methyl; Helicoverpa armigera nucleopolyhedrovirus; Heptamaloxyglucan; Ipconazole; Mandipropamid; Metaflumizone; Meptyldinocap; Novaluron; Orthosulfamuron; Paecilomyces fumosoroseus; Penoxsulam; Phosphane; Pinoxaden; Profoxydim; Proquinazid; *Pseudomonas* sp. Starin; Pseudozyma flocculosa; Pyridalyl; Pyroxsulam; Silver thiosulphate; Spinetoram; Spirodiclofen; Spiromesifen; Spirotetramat; Spodoptera littoralis nucleopolyhedrovirus; Tembotrione; Thiencarbazone; Topramezone; Trichoderma atroviride; Valiphenal; and Zucchini Yellow Mosaic Virus.

10. The oil dispersion according to claim 1 or claim 6 comprising as active ingredients at least one compound selected from the group consisting of: Acetamiprid, Thiacloprid, Thiamethoxam, Dinetofuran, Nitenpyram, Clothianidin; and at least one non-neonicotinoid pesticide selected from the group consisting of: 2,4-D; 2,4-DB; Alpha-Cypermethrin; Amitrole; Benalaxyl; Bentazone; Beta-Cyfluthrin; Bromoxynil; Carbendazim; Chlorothalonil; Chlorpropham; Chlorpyrifos; Chlorpyrifos-methyl; Chlorotoluron; Cyfluthrin; Cypermethrin; Daminozide; Deltamethrin; Desmedipham; Dinocap; Diquat; Esfenvalerate; Ethofumesate; Fluroxypyr; Flusilazole; Glyphosate; Imazalil; loxynil; Iprodione; Isoproturon; Lambda-Cyhalothrin; Linuron; Mancozeb; Maneb; MCPA; MCPB; Mecoprop-P; Metiram; Metsulfuron; Molinate; Pendimethalin; Phenmedipham; Propiconazole; Propineb; Propyzamide; Pyridate; Thiabendazole; Thifensulfuron; Thiophanate-methyl; Thiram; Triasulfuron; Warfarin; Ziram; Captan; Clodinafop; Clopyralid; Cyprodinil; Dichlorprop-P; Dimethoate; Dimethomorph; Diuron; Ethepon; Ethoprophos; Fenamiphos; Fipronil; Folpet; Formetanate; Fosetyl; Glufosinate; Metconazole; Methiocarb; Metribuzin; Oxamyl; Phosmet; Pirimicarb; Pirimiphos-methyl; Propamocarb; Pyrimethanil; Rimsulfuron; Tolclofos-methyl; Tolylfluanid; Tribenuron-methyl; Triclopyr; Trinexapac; Triticonazole; Abamectin; Avermectins; Aclonifen; Amidosulfuron; Benfluralin; Bensulfuron; Bifenox; Chloridazon; Clofentezine; Clomazone; Cymoxanil; Dicamba; Difenoconazole; Diflubenzuron; Diflufenican; Dodemorph; Epoxiconazole; Fenoxaprop-P; Fenpropidin; Fenpropimorph; Fenpyroximate; Fluazinam; Fludioxonil; Flutolanil; Fuberidazole; Imazaquin; Lenacil; Calcium phosphide; Magnesium phosphide; Mepiquat; Metamitron; Metazachlor; Nicosulfuron; Oxadiazon; Picloram; Prosulfocarb; Pyriproxyfen; Quinoclamine; Sodium 5-nitroguaiacolate; Sodium o-nitrophenolate; Sodium p-nitrophenolate; Sulcotrione; Tebuconazole; Tebufenpyrad;

Tralkoxydim; Triadimenol; Bacillus thuringiensis; Beauveria bassiana; Cydia pomonella granulosis virus; Lecanicillimu muscarium; Metarhizium anisopliae; Phlebiopsis gigantean; Pythium oligandrum; Streptomyces K61-Streptomyces griseoviridis; Trichoderma atroviride; Trichoderma harzianum Rifai; Trichoderma polysporum; Trichoderma aspellerum; Trichoderma gamsii; Verticillium albo-atrum; Ethylene; Gibberellic acid; Gibberellin; Pyrethrins; Acibenzolar-S-methyl-Benzothiadiazole; Ampelomyces quisqualis; Azimsulfuron; Azoxystrobin; Bacillus subtilis; Beflubutamid; Benthiavalicarb; Benzoic acid; Bifenazate; Boscalid; Carfentrazone-ethyl; Clothianidin; Coniothyrium minitans; Cyazofamid; Cyclanilide; Cyhalofop-butyl; Haloxyfop; Dimethenamid; Dimoxystrobin; Etoxazole; Ethoxysulfuron; Famoxadone; Fenamidone; Fenhexamid; Flazasulfuron; Florasulam; Flufenacet; Flumioxazin; Fluoxastrobin; Flupyrsulfuron methyl; Flurtamone; Foramsulfuron; Forchlorfenuron; Fosthiazate; Gliocladium catenulatum; Imazamox; Imazosulfuron; Indoxacarb; Iodosulfuron-methyl-sodium; Iprovalicarb; Isoxaflutole; Kresoxim-methyl; Laminarin; Mepanipyrim; Mesosulfuron; Mesotrione; Metalaxyl-M; Methoxyfenozide; Metrafenone; Milbemectin; Oxadiargyl; Oxasulfuron; Paecilomyces fumosoroseus; Paecilomyces lilacinus; Pethoxamid; Picolinafen; Picoxystrobin; Prohexadione-calcium; Propoxycarbazone; Prosulfuron; Prothioconazole; Pseudomonas chlororaphis; Pymetrozine; Pyraclostrobin; Pyraflufen-ethyl; Quinoxyfen; S-Metolachlor; Silthiofam; Spinosad; Spiroxamine; Spodoptera exigua nuclear polyhedrosis virus; Sulfosulfuron; Tepraloxydim; Trifloxystrobin; Tritosulfuron; Zoxamide; Bifenthrin; Etofenprox; Propaquizafop; Teflubenzuron; Tetraconazole; Triflusulfuron; Zeta-Cypermethrin; Chlormequat; Chlorsulfuron; Cyromazine; Dimethachlor; Diphenylamine; Lufenuron; Penconazole; Quizalofop-P; Triallate; Triazoxide Acequinocyl; Adoxophyes orana; Aminopyralid; Amisulbrom; Aureobasidium pullulans; Benalaxyl-M; Bispyribac sodium; Candida oleophila; Chlorantraniliprole; Chromafenozide; Cyflufenamid; Disodium phosphonate; Emamectin benzoate; FEN 560; Flonicamid; Flubendiamide; Fluopicolide; Gamma-cyhalothrin; Halosulfuron methyl; Helicoverpa armigera nucleopolyhedrovirus; Heptamaloxyglucan; Ipconazole; Mandipropamid; Metaflumizone; Meptyldinocap; Novaluron; Orthosulfamuron; Paecilomyces fumosoroseus; Penoxsulam; Phosphane; Pinoxaden; Profoxydim; Proquinazid; *Pseudomonas* sp. Starin; Pseudozyma flocculosa; Pyridalyl; Pyroxsulam; Silver thiosulphate; Spinetoram; Spirodiclofen; Spiromesifen; Spcirotetramat; Spodoptera littoralis nucleopolyhedrovirus; Tembotrione; Thiencarbazone; Topramezone; Trichoderma atroviride; Valiphenal; and Zucchini Yellow Mosaic Virus.

11. The oil dispersion according to claim 1 or claim 6 further, comprising suspended microcapsules enclosing neonicotinoids and optionally other pesticides, or an Emulsion Concentrate, Emulsion in Water, Suspension Concentrate in Water, Suspoemulsion containing neonicotinoids and optionally other pesticides.

12. The oil dispersion according to claim 1 or claim 6 further comprising microcapules enclosing at least one compound selected from the group consisting of: Spinosad, Abamectin, Methoprene, Buprofezin, Azadirachtin, Cyromazine, Fenoxycarb, Lambda-Cyhalothrin, Gamma-Cyhalothrin, Acrinathrin, Allethrin, Alpha-Cypermethrin, Beta-Cyfluthrin, Beta-Cypermethrin, Bifenthrin, Bioallethrin, Bioresmethrin, Cycloprothrin, Cyfluthrin, Cyhalothrin, Cypermethrin, Cyphenothrin, Deltamethrin, Empenthrin, Esfenvalerate, Fenpropathrin, Fenvalerate, Flucythrinate, Flumethrin, lmiprothrin, Methothrin, Permethrin, Phenothrin (1-R-trans), Prallethrin, Resmethrin, RU 15525, Tau-Fluvalinate, Tefluthrin, Tetramethrin (1-R), Theta-Cypermethrin, Tralomethrin, Transfluthrin, Zeta-Cypermethrin, ZXI 8901, Ethiprol, Fipronil, Bistrifluron, Chlorfluaturon, Diflubenzuron, Flucycloxuron, Flufenoxuron, Hexaflumuron, Lufenuron, Novaluron, Noviflumuron, Teflubezuron, Triflumuron, SZI-121, and microbial pesticides.

13. A method comprising the following step: providing an oil dispersion having a median particle size below 2 μm and a percentile 90 below 5 μm, when diluted in water and measured in a laser diffraction particle sizer, for killing or controlling pests that have nAChR receptor sites wherein the oil dispersion comprises, with regard to total weight of the oil dispersion formula:

a. At least a neonicotinoid, or mixtures thereof, at 0.5-40 wt.-%;

b. A mixture of nonionic polymeric oil dispersants made of polyethoxylated glycol ester of a (poly)hydroxylated fatty acid chain with 12-20 carbons at 0.5-8 wt.-% with a HLB of 4-6 and a copolymer of type A-B-A of fatty acid with a chain of 12-20 carbons at 0.5-5 wt.-%;

c. A mixture comprising polyethoxylated fatty alcohol at 0.5-15 wt.-%, and/or polypropoxylated fatty alcohol at 1-25 wt.-%, with a HLB of 12-16;

d. At least a polyethoxylated and/or polypropoxylated sorbitan derivative at 3-30 wt.-%, with a HLB of 12-16;

e. An alkylbenzenesulfonate sodium or calcium salt, being the alkyl chain of 10-14 carbon atoms, at 3-19 wt.-%;

f. A di-, tri- or tetra-valent cationic salt at 0.001 to 3 wt.-%;

g. An oil phase selected from the group consisting of paraffinic, naphtha aromatic, vegetable, synthetically modified vegetable oils and mixtures thereof, at 30-70 wt.-%; and h. Optionally, coformulants selected from the group consisting of non-ionic, anionic or cationic surface active ingredients, antioxidants, UV- and sun-light protectors, antimicrobial agents, pH regulators, viscosity modifiers, aluminium magnesium silicates, magnesium silicates, aluminosilicates, clays, modified clays, smectites, modified smectites, antifoam, colouring agents, and markers for traceability of the origin of the product.

14. The method of claim 13 comprising, referred to total weight percent of the oil dispersion formulation:

a. At least a neonicotinoid selected from Imidacloprid, Thiamethoxam, Thiacloprid, Nitenpyram, Acetamiprid, Clothianidin, Dinetofuran at 5-35 wt.-%;

b. A mixture of nonionic polymeric oil dispersants made of polyethoxylated glycol ester of a (poly) hydroxylated fatty acid chain with 12-20 carbons at 0.5-8 wt.-% with a HLB of 4-6 and a copolymer of type A-B-A of fatty acid with a chain of 12-20 carbons at 0.5-3 wt.-%;

c. A mixture made of 15-25 mols polyethoxylated stearyl alcohol at 0.5-10 wt.-%, 15-25 mols polyethoxylated oleyl alcohol at 0.5-10 wt.-% and 10-20 mols polypropoxylated monostearyl ether at 1-15 wt.-%, with a HLB of 12-16;

d. A mixture made of 15-25 mols polyethoxylated sorbitan trioleate or tristearate at 5-20 wt.-% and 20-50 mols polyethoxylated sorbitan hepta-9-octadecenoate at 2-20 wt.-%, with a HLB of 12-16;

e. Calcium or sodium dodecylbenzenesulfonate at 8-19 wt.-%;

f. A paraffinic or vegetable oil at 30-70 wt.-%;

g. Aluminium sulfate in anhydrous, monohydrate or any hydrated state at 0.005 to 0.3 wt.-%; and i. An organomodified smectite at 0.3-3 wt.-%.

* * * * *